United States Patent
Shima et al.

(10) Patent No.: US 10,215,766 B2
(45) Date of Patent: Feb. 26, 2019

(54) BLOOD SAMPLE DETERMINATION METHOD AND BLOOD SAMPLE ANALYZER

(71) Applicants: PUBLIC UNIVERSITY CORPORATION NARA MEDICAL UNIVERSITY, Kashihara-shi, Nara (JP); SYSMEX CORPORATION, Kobe-shi, Hyogo (JP)

(72) Inventors: Midori Shima, Kashihara (JP); Keiji Nogami, Kashihara (JP); Yuka Tabuchi, Kobe (JP); Hiroshi Kurono, Kobe (JP)

(73) Assignees: PUBLIC UNIVERSITY CORPORATION NARA MEDICAL UNIVERSITY, Kashihara-shi, Nara (JP); SYSMEX CORPORATION, Kobe-shi, Hyogo (JP)

( * ) Notice: Subject to any disclaimer, the term of this patent is extended or adjusted under 35 U.S.C. 154(b) by 238 days.

(21) Appl. No.: 14/969,698

(22) Filed: Dec. 15, 2015

(65) Prior Publication Data

US 2016/0178651 A1   Jun. 23, 2016

(30) Foreign Application Priority Data

Dec. 19, 2014   (JP) ................................ 2014-257531

(51) Int. Cl.
*G01N 33/86*   (2006.01)
*G01N 33/49*   (2006.01)
*G01N 21/49*   (2006.01)
*G01N 21/75*   (2006.01)
*G01N 21/82*   (2006.01)

(52) U.S. Cl.
CPC ......... *G01N 33/86* (2013.01); *G01N 33/4905* (2013.01); *G01N 21/49* (2013.01);
(Continued)

(58) Field of Classification Search
CPC ....... G01N 2021/825; G01N 2800/224; G01N 33/86; G01N 33/48; G01N 33/49;
(Continued)

(56) References Cited

U.S. PATENT DOCUMENTS

2003/0104493 A1   6/2003   Ortel et al.
2004/0248308 A1*  12/2004  Toh ........................ G01N 33/86
                                                                     436/69

(Continued)

OTHER PUBLICATIONS

English translation of the printed summary of "Usefulness of clot waveform analysis in diagnosis of hemophilia A and antiphospholipid syndrome", Tomoko Matsumoto, Keiji Nogami, Midori Shima, Department of Pediatrics, Nara Medical University, 1 page.

(Continued)

*Primary Examiner* — Maureen Wallenhorst
(74) *Attorney, Agent, or Firm* — Sughrue Mion, PLLC

(57) ABSTRACT

Disclosed is a blood sample determination method including: emitting light to a measurement specimen prepared by mixing a clotting time measuring reagent and a blood sample suspected to be derived from a subject having lupus anticoagulant or a coagulation factor inhibitor, to obtain optical information about an amount of light from the measurement specimen; obtaining at least one parameter regarding derivative of clot waveform, based on the obtained optical information; and determining, based on a value of the obtained parameter, whether the blood sample is suspected to be a sample derived from a subject having lupus anticoagulant or is suspected to be a sample derived from a subject having a coagulation factor inhibitor.

10 Claims, 16 Drawing Sheets

(52) U.S. Cl.
CPC ............. *G01N 21/75* (2013.01); *G01N 21/82* (2013.01); *G01N 2021/825* (2013.01); *G01N 2800/224* (2013.01)

(58) Field of Classification Search
CPC .... G01N 33/4905; G01N 21/47; G01N 21/49; G01N 21/59
USPC ............. 436/63, 69, 164; 435/13, 29, 288.7; 422/73, 82.05, 82.09; 73/64.41, 64.43; 600/369
See application file for complete search history.

(56) References Cited

U.S. PATENT DOCUMENTS

2013/0344519 A1\* 12/2013 Leong .................... G01N 33/86
435/13
2016/0291042 A1\* 10/2016 Kumano ............ G01N 33/4905

OTHER PUBLICATIONS

English translation of slides used in oral presentation, "Usefulness of Clot Waveform Analysis in Diagnosis of Hemophilia A and Antiphospholipid Syndrome", Department of Pediatrics, Nara Medical University, Tomoko Matsumoto, Keiji Nogami, Midori Shima, Fifteenth Annual Meeting of the Japanese Society for Laboratory Hematology, Jul. 21, 2014.
M. Shima et al., "Towards standardization of clot waveform analysis and recommendations for its clinical applications", Journal of Thrombosis and Haemostasis, 2013, pp. 1417-1420, vol. 11.

\* cited by examiner

BLOOD SAMPLE DETERMINATION METHOD AND BLOOD SAMPLE ANALYZER

CROSS REFERENCE TO RELATED APPLICATIONS

This application claims priority from prior Japanese Patent Application No. 2014-257531, filed on Dec. 19, 2014, entitled "Method, system, and computer program for blood sample determination, and blood sample analyzer", the entire content of which is incorporated herein by reference.

FIELD OF THE INVENTION

The present invention relates to a method for blood sample determination. The present invention also relates to a system and a computer program for blood sample determination. Further, the present invention relates to a blood sample analyzer.

BACKGROUND

Coagulation test, which is one type of blood test, is conducted by measuring the clotting time of blood in order to grasp the state of hemostasis mechanism. When prolongation of clotting time is observed, congenital coagulation disorder due to congenital deficiency or abnormality in blood coagulation factors, or acquired coagulation inhibition due to autoantibodies or drugs, e.g. warfarin, that inhibit coagulation reaction is suspected as the cause of the prolongation. Congenital coagulation disorder can be distinguished from acquired coagulation inhibition based on a test (cross-mixing test) that measures the clotting time of a specimen prepared by mixing normal plasma and test plasma (i.e., plasma to be tested) showing prolongation of the clotting time. That is, in the case of congenital coagulation disorder, prolongation of the clotting time is corrected by the test plasma being mixed with normal plasma, but in the case of acquired coagulation disorder, prolongation of the clotting time is not corrected.

With respect to acquired coagulation disorder caused by autoantibodies, it is known that the pathological conditions are different depending on the kinds of the autoantibodies. For example, patients having autoantibodies against blood coagulation factors (also referred to as coagulation factor inhibitors) show bleeding symptoms in general. On the other hand, in the case of an autoantibody called lupus anticoagulant (LA), it inhibits phospholipids that are necessary for phospholipid-dependent coagulation reaction, but patients having LA show thrombus symptoms. Therefore, distinguishing a sample containing a coagulation factor inhibitor from a sample containing LA is clinically important. However, as described above, since both samples show prolongation of clotting time, it is difficult for an ordinary coagulation test to distinguish them from each other. Thus, for this distinction, it is necessary to separately conduct a test or the like that detects coagulation factor inhibitors or LA.

On the other hand, in recent years, for assessment of the entire process from the start of clotting to formation of fibrin clots, analysis of clot waveform has been attracting attention. The clot waveform is a waveform that represents temporal change in optical characteristics such as transmission and scatter of light in the sample, the change occurring in accordance with advancement of blood sample clotting. Through the analysis of the clot waveform, information such as velocity and acceleration of coagulation is obtained. For example, US2003/0104493 describes that patients having antiphospholipid antibodies (including LA) and receiving warfarin showed maximum coagulation acceleration and maximum coagulation deceleration that are different from those of healthy individuals. A document titled "Towards standardization of clot waveform analysis and recommendations for its clinical applications", by Shima M. et al., J Thromb Haemost, 2013, vol. 11, p. 1417-1420 describes the following: clot waveform analysis was conducted on acquired hemophilia A, which is a disease in which the activity of factor VIII is decreased by factor VIII inhibitor; and it was found that samples derived from acquired hemophilia A are characterized by their lower values of maximum coagulation velocity and maximum coagulation acceleration than those of normal samples.

SUMMARY OF THE INVENTION

The scope of the present invention is defined solely by the appended claims, and is not affected to any degree by the statements within this summary.

As described above, in an ordinary coagulation test, it is difficult to distinguish a blood sample containing a coagulation factor inhibitor from a blood sample containing LA. Thus, it is necessary to conduct another test, which takes time before obtaining results. In addition, with a test which discerns the patterns of changes in measurement data to distinguish the above-types of blood samples from each other, there are cases only experts can make the determination. Therefore, there are demands for means that allow simple determination, by use of a clotting time measuring reagent usually used in a coagulation test, on whether the blood sample is suspected to be a sample derived from a subject having lupus anticoagulant, or is suspected to be a sample derived from a subject having a coagulation factor inhibitor.

A first aspect of the present invention provides a blood sample determination method. This blood sample determination method includes: emitting light to a measurement specimen prepared by mixing a clotting time measuring reagent and a blood sample suspected to be derived from a subject having LA or a coagulation factor inhibitor, to obtain optical information about an amount of light from the measurement specimen; obtaining at least one parameter regarding derivative of clot waveform, based on the obtained optical information; and determining, based on a value of the obtained parameter, whether the blood sample is suspected to be a sample derived from a subject having LA or is suspected to be a sample derived from a subject having a coagulation factor inhibitor.

A second aspect of the present invention provides a blood sample determination method. This blood sample determination method includes: emitting light to a measurement specimen prepared by mixing a blood sample and a clotting time measuring reagent, to obtain optical information about an amount of light from the measurement specimen; obtaining a clotting time and obtaining at least one parameter regarding derivative of clot waveform, based on the obtained optical information; and with respect to a blood sample for which prolongation of the clotting time is observed, determining, based on a value of the obtained parameter, whether the blood sample is suspected to be a sample derived from a subject having LA or is suspected to be a sample derived from a subject having a coagulation factor inhibitor.

A third aspect of the present invention provides a blood sample analyzer. This blood sample analyzer includes: an optical information obtaining unit configured to emit light to a measurement specimen prepared by mixing a blood sample and a clotting time measuring reagent, to obtain optical information about an amount of light from the measurement specimen; and a controller programmed to perform operation including: obtaining, based on the optical information, at least one parameter selected from the group consisting of maximum coagulation velocity (|min 1|), maximum coagulation acceleration (|min 2|), and maximum coagulation deceleration (max 2), and the controller is programmed to perform operation including: comparing a value of the obtained parameter with a predetermined threshold, and outputting reference information about the blood sample based on a result of the comparison.

A fourth aspect of the present invention provides a system for blood sample determination, including a computer which includes a processor and a memory under control of the processor. The memory has stored therein a computer program which causes the computer to execute operation including: obtaining optical information about an amount of light from a measurement specimen prepared by mixing a blood sample and a clotting time measuring reagent; obtaining at least one parameter regarding derivative of clot waveform, based on the obtained optical information; and determining, based on a value of the obtained parameter, whether the blood sample is suspected to be a sample derived from a subject having LA or is suspected to be a sample derived from a subject having a coagulation factor inhibitor.

A fifth aspect of the present invention provides a computer program for blood sample determination stored in a computer-readable medium. This computer program causes the computer to execute operations including: obtaining optical information about an amount of light from a measurement specimen prepared by mixing a blood sample and a clotting time measuring reagent; obtaining at least one parameter regarding derivative of clot waveform, based on the obtained optical information; and determining, based on a value of the obtained parameter, whether the blood sample is suspected to be a sample derived from a subject having LA or is suspected to be a sample derived from a subject having a coagulation factor inhibitor.

DETAILED DESCRIPTION OF THE PREFERRED EMBODIMENTS

[1. Blood Sample Determination Method]

Figure 1:
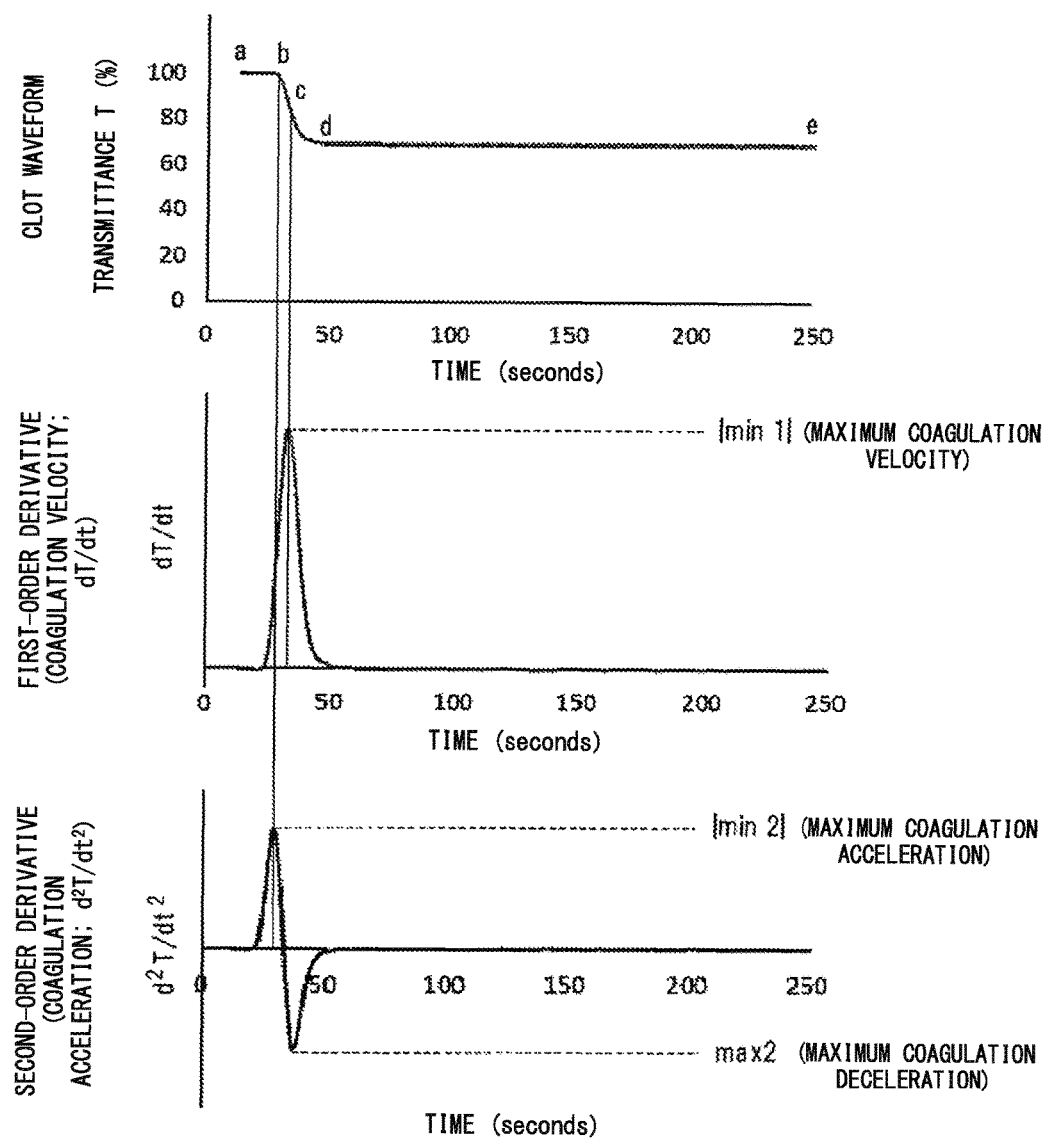
FIG. 1 is one example of graphs of the clot waveform of normal plasma, a first-order derivative thereof, and a second-order derivative thereof.

In a blood determination method according to a first aspect (hereinafter, also simply referred to as "method"), first, light is emitted to a measurement specimen prepared by mixing a clotting time measuring reagent and a blood sample suspected to be derived from a subject having LA or a coagulation factor inhibitor, and optical information about the amount of light is obtained from the measurement specimen.

The blood sample is not limited to a particular one as long as it is a sample suspected to be derived from a subject having LA or a coagulation factor inhibitor. Examples of such samples include a group of samples obtained from a plurality of subjects including persons having LA and/or persons having coagulation factor inhibitors. Alternatively, the blood sample may be a blood sample a portion of which has been subjected to a coagulation test in advance and which has been confirmed to have a prolonged clotting time. The kind of the blood sample may be whole blood or plasma, and preferably, is plasma. To the blood sample, a known anticoagulant agent usually used in a coagulation test may have been added. Examples of such anticoagulant agents include trisodium citrate.

In the present embodiment, it is sufficient that the clotting time measuring reagent (hereinafter, also simply referred to as "reagent") is a reagent for measuring clotting time based on a known measurement principle in this technical field. Examples of such a reagent include a reagent for measuring at least one of prothrombin time, activated partial thromboplastin time, dilute prothrombin time, dilute activated partial thromboplastin time, kaolin clotting time, dilute Russell's Viper Venom time, thrombin time, and dilute thrombin time. A clotting time measuring reagent and a reagent kit which are commercially available may be used.

In the present embodiment, it is sufficient that the measurement specimen is prepared by mixing a blood sample and the reagent by a known technique in accordance with the measurement principle of the reagent to be used. The reaction time of the blood sample and the reagent is normally not shorter than |minute and not longer than 10 minutes, and preferably, not shorter than 3 minutes and not longer than 5 minutes. The temperature condition is normally not lower than 25° C. and not higher than 45° C., and preferably, not lower than 35° C. and not higher than 38° C. The measurement specimen may be prepared by hand or by a fully automated measurement apparatus. Examples of such an apparatus include CS series (Sysmex Corporation) of fully automated blood coagulation measurement apparatuses, for example.

In the present embodiment, it is sufficient that light to be emitted to the measurement specimen is light that is usually used in measurement of clotting time. Examples of such light include light whose wavelength is about 660 nm, and preferably, 660 nm. The light source is not limited to a particular one, but examples of the light source include a light-emitting diode and a halogen lamp.

By emitting light from the above light source to a measurement specimen, scattered light and transmitted light occur at the measurement specimen. In the present embodiment, examples of optical information about the amount of light include information about the amount of scattered light or the amount of transmitted light, and scattered light intensity, transmittance, absorbance, or the like is preferred.

In the present embodiment, the measurement condition is not limited to a particular one. Preferably, emission of light and obtainment of the optical information about the amount of light are continuously or intermittently performed after the mixing of the blood sample and the reagent (immediately after the preparation of the measurement specimen) until the end of coagulation reaction (formation of fibrin clots). Based on the optical information about the amount of light (for example, scattered light intensity, transmittance, or absorbance) continuously or intermittently measured through the entire process of the coagulation, it is possible to obtain parameters regarding derivative of clot waveform described later, at a desired time point or during a desired time period in the coagulation process. Emission of light and obtainment of optical information about the amount of light may be performed by a fully automated measurement apparatus. Examples of such an apparatus include the CS series (Sysmex Corporation) of fully automated blood coagulation measurement apparatuses.

Next, in the method according to the present embodiment, at least one parameter regarding derivative of clot waveform is obtained based on the obtained optical information.

In the present embodiment, the clot waveform is a waveform that represents temporal change in optical information about the amount of light in the coagulation process of a measurement specimen prepared by mixing a blood sample and a clotting time measuring reagent, the information being obtained by optically measuring the measurement specimen. With reference to FIG. 1, the clot waveform and analysis of the waveform will be described. In the clot waveform (the uppermost graph) in FIG. 1, Point a indicates the measurement start point (immediately after the preparation of the measurement specimen), Point b indicates the fibrin deposition (coagulation start) point, and a-b indicates the clotting time. Point c is the midpoint of the coagulation, Point d is the end point of the coagulation, and Point e is the end point of the measurement. When derivative of the clot waveform is taken (first-order derivative), coagulation velocity is calculated (see the middle graph in FIG. 1). It should be noted that Point c in the clot waveform corresponds to the maximum value of the first-order derivative. When derivative of the coagulation velocity is taken (second-order derivative), coagulation acceleration is calculated (see the lowermost graph in FIG. 1). It should be noted that, in the method according to the present embodiment, determination is made by use of parameters regarding derivative of clot waveform described later, and thus, obtainment of the clotting time and the clot waveform may or may not be performed.

In the present embodiment, the parameter regarding derivative of clot waveform is not limited to a particular one as long as the parameter is a value that indicates at least one of coagulation velocity, coagulation acceleration, and coagulation deceleration, which are obtained based on the obtained optical information. Here, the value indicating the coagulation velocity corresponds to a value that can be obtained from the first-order derivative of clot waveform, and the value indicating the coagulation acceleration and the value indicating the coagulation deceleration correspond to values that can be obtained from the second-order derivative of clot waveform. Examples of such a parameter include |min 1|, |min 2|, and max 2. The |min 1| is the absolute value of the minimum value of the first-order derivative of clot waveform, and represents maximum coagulation velocity. The |min 2| is the absolute value of the minimum value of the second-order derivative of clot waveform, and represents maximum coagulation acceleration. The max 2 is the maximum value of the second-order derivative of clot waveform, and represents maximum coagulation deceleration. The term |min 1|, |min 2|, and max 2 themselves are known in this technical field. The parameter regarding derivative of clot waveform may be a value that can be obtained by combining two or more of these values. Examples of such a parameter include the sum, the difference, the product, the ratio of at least two values selected from |min 1|, |min 2|, and max 2.

In a case where the clotting time has also been obtained, the parameter regarding derivative of clot waveform may be a value obtained by combining the clotting time and a value obtained from the first-order derivative or the second-order derivative of clot waveform. Examples of such a value include the sum, the difference, the product, and the ratio of the value of the clotting time and at least one value selected from |min 1|, |min 2|, and max 2.

In the method according to the present embodiment, based on the value of the obtained parameter, it is determined whether the blood sample is suspected to be a sample derived from a subject having LA or is suspected to be a sample derived from a subject having a coagulation factor inhibitor.

In the present embodiment, preferably, the determination is made based on the result of comparison of the value of the obtained parameter with a predetermined threshold corresponding to the parameter. For example, the value of |min 1| is compared with a first threshold in a case where |min 1| has been obtained, the value of |min 2| is compared with a second threshold in a case where |min 2| has been obtained, and the value of max 2 is compared with a third threshold in a case where max 2 has been obtained. Then, based on the result of the comparison, the determination can be made. For example, when at least one of the values that have been obtained among |min 1|, |min 2|, and max 2 is greater than or equal to the predetermined threshold corresponding to that value, it can be determined that the blood sample is suspected to be a sample derived from a subject having LA. On the other hand, when all the values that have been obtained among |min 1|, |min 2|, and max 2 are smaller than the predetermined thresholds corresponding to those values, it can be determined that the blood sample is suspected to be a sample derived from a subject having a coagulation factor inhibitor.

In a case where any one of |min 1|, |min 2|, and max 2 has been obtained as the parameter regarding derivative of clot waveform, the determination can be made as follows, for example:

The value of |min 1| is compared with the first threshold. Then, when the value of |min 1| is greater than or equal to the first threshold, it is determined that the blood sample is suspected to be a sample derived from a subject having LA. On the other hand, when the value of |min 1| is smaller than the first threshold, it is determined that the blood sample is suspected to be a sample derived from a subject having a coagulation factor inhibitor.

The value of |min 2| is compared with the second threshold. Then, when the value of |min 2| is greater than or equal to the second threshold, it is determined that the blood sample is suspected to be a sample derived from a subject having LA. On the other hand, when the value of |min 2| is smaller than the second threshold, it is determined that the blood sample is suspected to be a sample derived from a subject having a coagulation factor inhibitor.

The value of max 2 is compared with the third threshold. Then, when the value of max 2 is greater than or equal to the third threshold, it is determined that the blood sample is suspected to be a sample derived from a subject having LA. On the other hand, when the value of max 2 is smaller than the third threshold, it is determined that the blood sample is suspected to be a sample derived from a subject having a coagulation factor inhibitor.

In a case where any two of |min 1|, |min 2|, and max 2 have been obtained as the parameter regarding derivative of clot waveform, the determination can be made as follows, for example:

The value of |min 1| is compared with the first threshold, and the value of |min 2| is compared with the second threshold. Then, when the value of |min 1| is greater than or equal to the first threshold, or the value of |min 2| is greater than or equal to the second threshold, it is determined that the blood sample is suspected to be a sample derived from a subject having LA. On the other hand, when the value of |min 1| is smaller than the first threshold and the value of |min 2| is smaller than the second threshold, it is determined that the blood sample is suspected to be a sample derived from a subject having a coagulation factor inhibitor.

The value of |min 1| is compared with the first threshold, and the value of max 2 is compared with the third threshold. Then, when the value of |min 1| is greater than or equal to the first threshold or the value of max 2 is greater than or equal to the third threshold, it is determined that the blood sample is suspected to be a sample derived from a subject having LA. On the other hand, when the value of |min 1| is smaller than the first threshold and the value of max 2 is smaller than the third threshold, it is determined that the blood sample is suspected to be a sample derived from a subject having a coagulation factor inhibitor.

The value of |min 2| is compared with the second threshold, and the value of max 2 is compared with the third threshold. Then, when the value of |min 2| is greater than or equal to the second threshold, or the value of max 2 is greater than or equal to the third threshold, it is determined that the blood sample is suspected to be a sample derived from a subject having LA. On the other hand, when the value of |min 2| is smaller than the second threshold and the value of max 2 is smaller than the third threshold, it is determined that the blood sample is suspected to be a sample derived from a subject having a coagulation factor inhibitor.

In a case where three of |min 1|, |min 2|, and max 2 have been obtained as the parameter regarding derivative of clot waveform, the determination can be made as follows, for example:

The value of |min 1| is compared with the first threshold, the value of |min 2| is compared with the second threshold, and the value of max 2 is compared with the third threshold. Then, when the value of |min 1| is greater than or equal to the first threshold, or the value of |min 21 is greater than or equal to the second threshold, or the value of max 2 is greater than or equal to the third threshold, it is determined that the blood sample is suspected to be a sample derived from a subject having LA. On the other hand, when the value of |min 1| is smaller than the first threshold, and the value of |min 2| is smaller than the second threshold, and the value of max 2 is smaller than the third threshold, it is determined that the blood sample is suspected to be a sample derived from a subject having a coagulation factor inhibitor.

In the present embodiment, the predetermined thresholds are not limited to particular ones. For example, by accumulating data of various parameters regarding derivative of clot waveform with respect to LA positive samples and coagulation factor inhibitor positive samples, it is possible to empirically set predetermined thresholds corresponding to the respective parameters. Alternatively, with respect to each of a LA positive sample group and a coagulation factor inhibitor positive sample group, values of various parameters regarding derivative of clot waveform are obtained, and values that each can clearly separate the groups from each other may be set as the predetermined thresholds.

In another embodiment, with respect to each blood sample, a clotting time is obtained in addition to the parameter regarding derivative of clot waveform, and with respect to a blood sample for which prolongation of the clotting time is observed, the above determination may be made. In this embodiment, based on the clotting time, it is possible to select and determine a blood sample that is suspected to be derived from a subject having LA or a coagulation factor inhibitor. A blood sample determination method according to this embodiment (second aspect) will be described below.

In the present embodiment, the blood sample is not limited to a particular one as long as the blood sample is blood or plasma. In the present embodiment, details of the clotting time measuring reagent, preparation of the measurement specimen, and obtainment of optical information about the amount of light are the same as those described with regard to the method according to the first aspect.

In the present embodiment, based on the obtained optical information, the clotting time is obtained and at least one parameter regarding derivative of clot waveform is obtained. Details of obtainment of the parameter regarding derivative of clot waveform are the same as those in described with regard to the method according to the first aspect. The method for obtaining the clotting time itself is known in this technical field. Thus, persons skilled in the art can obtain as appropriate the clotting time of a blood sample in accordance with the measurement principle of the clotting time measuring reagent to be used.

In the present embodiment, with respect to a blood sample for which prolongation of the clotting time has been observed, it is determined, based on the value of the obtained parameter, whether the blood sample is suspected to be a sample derived from a subject having LA or is suspected to be a sample derived from a subject having a coagulation factor inhibitor. Details of the procedure of the determination and the predetermined thresholds corresponding to the respective parameters are the same as those described with regard to the method according to the first aspect.

In the present embodiment, preferably, whether the clotting time of the blood sample has been prolonged is determined based on the result of comparison of the obtained clotting time with a predetermined clotting time. For example, when the obtained clotting time is longer than the predetermined clotting time, it can be determined that the blood sample is a sample for which prolongation of the clotting time is observed. On the other hand, when the obtained clotting time is not longer than the predetermined clotting time, it can be determined that the blood sample is a sample for which prolongation of the clotting time is not observed.

Preferably, the predetermined clotting time is the clotting time of a normal sample. An example of the normal sample is blood or plasma derived from a healthy individual. Alternatively commercially available normal plasma may be used. The clotting time of such a normal sample may be the clotting time thereof actually measured in the same manner as in the case of the blood sample. Alternatively, the clotting time of such a normal sample may be a clotting time known as a normal value or a reference value in the measurement principle of the clotting time measuring reagent to be used.

In the present embodiment, it is considered that the blood sample for which prolongation of the clotting time is not observed is not suspected to be derived from a subject having LA or coagulation factor inhibitor.

[2. Blood Sample Analyzer, System, and Computer Program]

Figure 2:
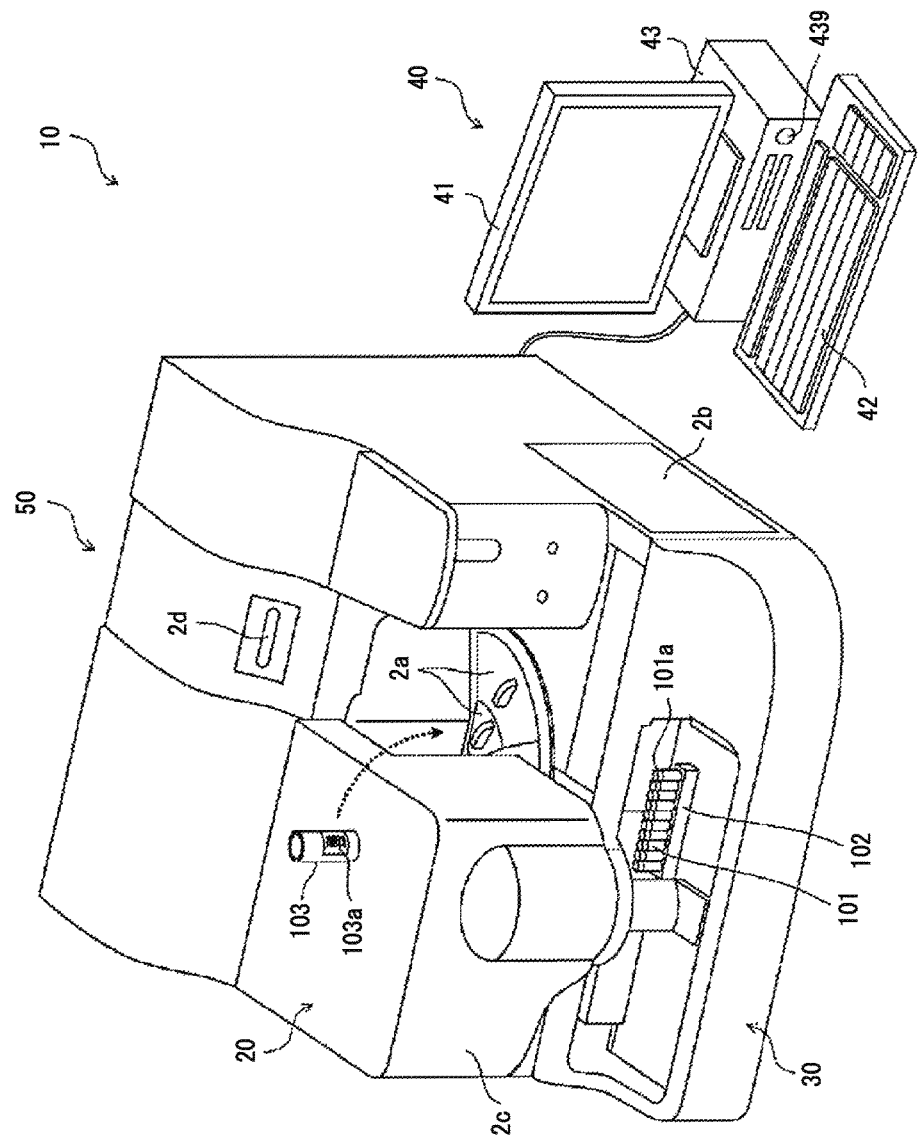
FIG. 2 is a perspective view showing an external structure of a blood sample analyzer.

One example of a blood sample analyzer of the present embodiment will be described below with reference to the drawings. However, the present embodiment is not limited to this example. As shown in FIG. 2, a blood sample analyzer 10 includes: a measurement unit 20 which obtains optical information about the amount of light from a measurement specimen; a sample transport unit 30 disposed to the front of the measurement unit 20; and a control device 40 which analyzes measurement data obtained by the measurement unit 20 and gives instructions to the measurement unit 20. The measurement unit 20 and the sample transport unit 30 form an optical information obtaining unit 50.

The measurement unit 20 is provided with lids 2a and 2b, a cover 2c, and a power button 2d. A user can open the lid 2a to replace reagent containers 103 set on reagent tables 11 and 12 (see FIG. 3) with new reagent containers 103, or to newly add other reagent containers 103. Each reagent container 103 has a bar code label 103a attached thereto. On the bar code label 103a, a bar code including the kind of the reagent contained therein and a reagent ID composed of a serial number given to the reagent are printed.

Figure 3:
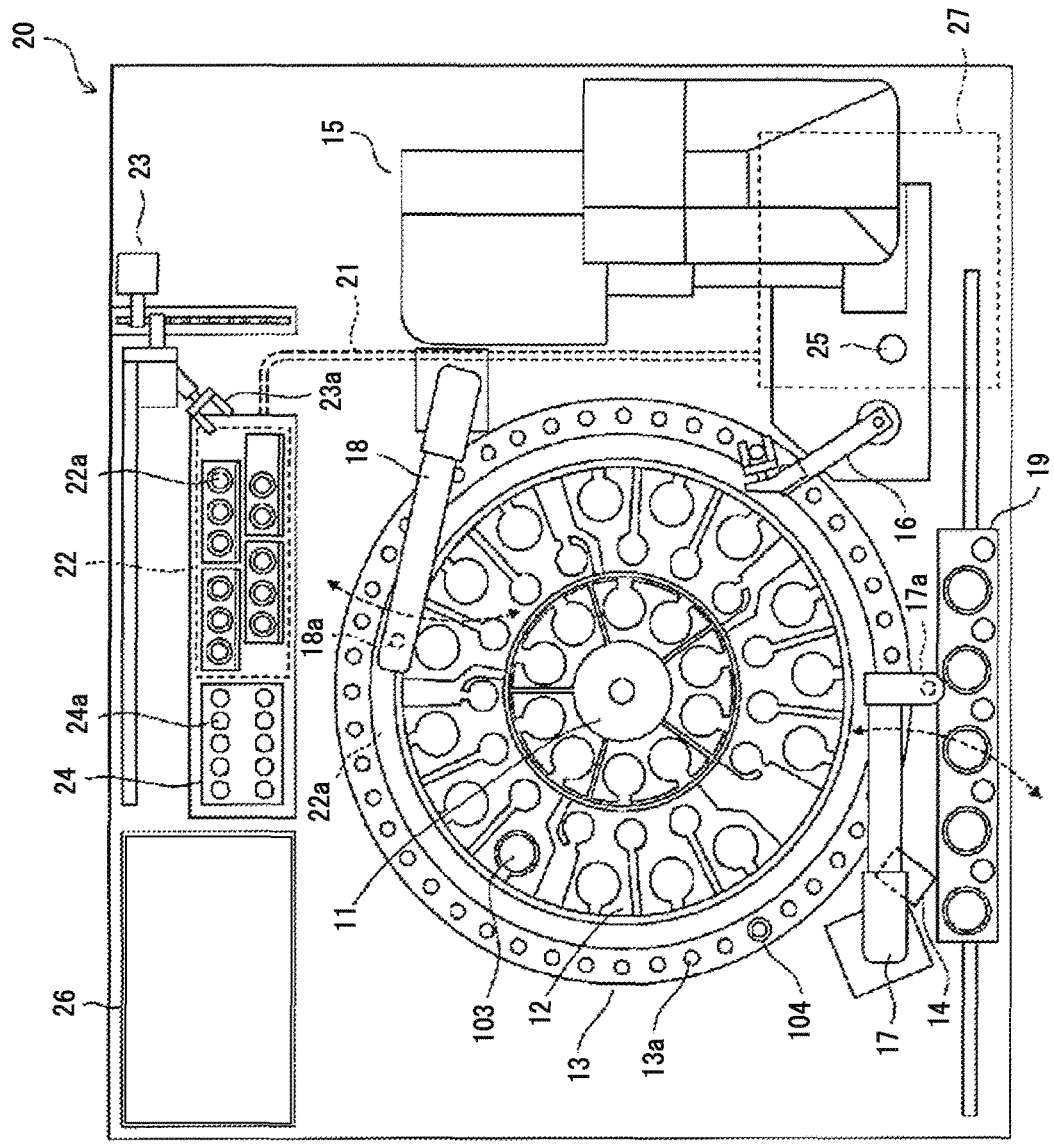
FIG. 3 is a plan view showing the inside of a measurement unit of the blood sample analyzer viewed from above.

The user can open the lid 2b to replace a lamp unit 27 (see FIG. 3). The user can open the cover 2c to replace a piercer 17a (see FIG. 3). The sample transport unit 30 transports a sample container 101 supported by a sample rack 102, to an aspiration position for the piercer 17a. The sample container 101 is sealed by a cap 101a made of rubber.

When using the blood sample analyzer 10, the user first presses the power button 2d of the measurement unit 20 to activate the measurement unit 20, and presses a power button 439 of the control device 40 to activate the control device 40. Upon activation of the control device 40, a log-on screen is displayed on a display unit 41. The user inputs a user name and a password on the log-on screen to log on the control device 40, and starts using the blood sample analyzer 10.

As shown in FIG. 3, the measurement unit 20 includes the reagent tables 11 and 12, a cuvette table 13, a bar code reader 14, a cuvette supply unit 15, a catcher 16, a sample dispensing arm 17, a reagent dispensing arm 18, an urgent sample setting part 19, an optical fiber 21, a detection unit 22, a cuvette transfer unit 23, a heating unit 24, a discard hole 25, a fluid unit 26, and the lamp unit 27.

Each of the reagent tables 11 and 12 and the cuvette table 13 has an annular shape and is rotatable. Reagent containers 103 are placed on the reagent tables 11 and 12. The bar code of each of the reagent containers 103 placed on the reagent tables 11 and 12 is read by the bar code reader 14. Information (kind of reagent and reagent ID) read from the bar code is inputted to the control device 40, to be stored in a hard disk 434 (see FIG. 6).

The cuvette table 13 has support parts 13a formed therein which are a plurality of holes capable of supporting cuvettes 104 therein. New cuvettes 104 loaded by the user into the cuvette supply unit 15 are sequentially transferred by the cuvette supply unit 15, to be set in the support parts 13a of the cuvette table 13 by the catcher 16.

Stepping motors are connected to each of the sample dispensing arm 17 and the reagent dispensing arm 18 so that the sample dispensing arm 17 and the reagent dispensing arm 18 can move in up-down directions and rotate. At the tip of the sample dispensing arm 17, the piercer 17a is provided whose tip is formed sharp so as to be able to puncture the cap 101a of each sample container 101. At the tip of the reagent dispensing arm 18, a pipette 18a is provided. Different from the piercer 17a, the tip of the pipette 18a is formed flat. A liquid surface detection sensor 213 of a capacitance type (see FIG. 4) is connected to the pipette 18a.

The lamp unit 27 supplies light having a plurality of kinds of wavelengths to be used in detection of optical signals performed by the detection unit 22. The light from the lamp unit 27 is supplied to the detection unit 22 via the optical fiber 21. The detection unit 22 is provided with a plurality of support parts 22a each having a hole shape. A cuvette 104 can be inserted into each support part 22a. To each support part 22a, an end of the optical fiber 21 is attached. Accordingly, light from the optical fiber 21 can be emitted to the cuvette 104 supported in the support part 22a. The detection unit 22 emits, to the cuvette 104, light supplied from the lamp unit 27 via the optical fiber 21. The detection unit 22 detects the amount of light that has transmitted through the cuvette 104 (or the amount of scattered light from the cuvette 104).

When a sample container 101 has been transported to a predetermined position by the sample transport unit 30 (see FIG. 2), the piercer 17a is located immediately above the sample container 101 by rotation of the sample dispensing arm 17. Then, the sample dispensing arm 17 is moved downwardly, the piercer 17a pierces the cap 101a of the sample container 101, and then, the blood sample contained in the sample container 101 is aspirated by the piercer 17a. In a case where an urgent blood sample is set in the urgent sample setting part 19, the piercer 17a aspirates the urgent blood sample by interrupting the samples supplied from the sample transport unit 30. The blood sample aspirated by the piercer 17a is discharged into an empty cuvette 104 on the cuvette table 13.

The cuvette 104 into which the blood sample has been discharged is transferred by a catcher 23a of the cuvette transfer unit 23, from the support part 13a of the cuvette table 13 to a support part 24a of the heating unit 24. The heating unit 24 heats the blood sample contained in the cuvette 104 set in the support part 24a to a predetermined temperature (37° C., for example). When the heating of the blood sample by the heating unit 24 ends, this cuvette 104 is gripped again by the catcher 23a. Then, this cuvette 104 is located to a predetermined position while being gripped by the catcher 23a. In this state, the reagent aspirated by the pipette 18a is discharged into the cuvette 104.

In the dispensing of the reagent by the pipette 18a, first, the reagent tables 11 and 12 are rotated. Then, a reagent container 103 which contains the reagent corresponding to the measurement item is transported to the aspiration position for the pipette 18a. Then, after the position in the up-down direction of the pipette 18a has been set at the origin position based on a sensor for detecting the origin position, the pipette 18a is lowered until the liquid surface detection sensor 213 detects that the lower end of the pipette 18a has come into contact with the liquid surface of the reagent. When the lower end of the pipette 18a has come into contact with the liquid surface of the reagent, the pipette 18a is further lowered to an extent that allows aspiration of the reagent by a necessary amount. Then, the lowering of the pipette 18a is stopped, and the reagent is aspirated by the pipette 18a. The reagent aspirated by the pipette 18a is discharged into the cuvette 104 gripped by the catcher 23a. Then, by the vibration function of the catcher 23a, the blood sample and the reagent in the cuvette 104 are stirred. Accordingly, a measurement specimen is prepared.

Thereafter, the cuvette 104 containing the measurement specimen is transferred to a support part 22a of the detection unit 22 by the catcher 23a. As described above, the detection unit 22 emits, to the cuvette 104, light supplied from the lamp unit 27, to obtain optical information from the measurement specimen. The obtained optical information is transmitted to the control device 40. The control device 40 performs analysis based on the optical information, and displays the analysis result on the display unit 41.

After the measurement ends, the cuvette 104 that is no more needed is transported by the cuvette table 13, to be discarded into the discard hole 25 by the catcher 16. It should be noted that during the measurement operation, the piercer 17a and the pipette 18a are each cleaned as appropriate by a liquid such as a cleaning liquid supplied from the fluid unit 26.

Figure 4:
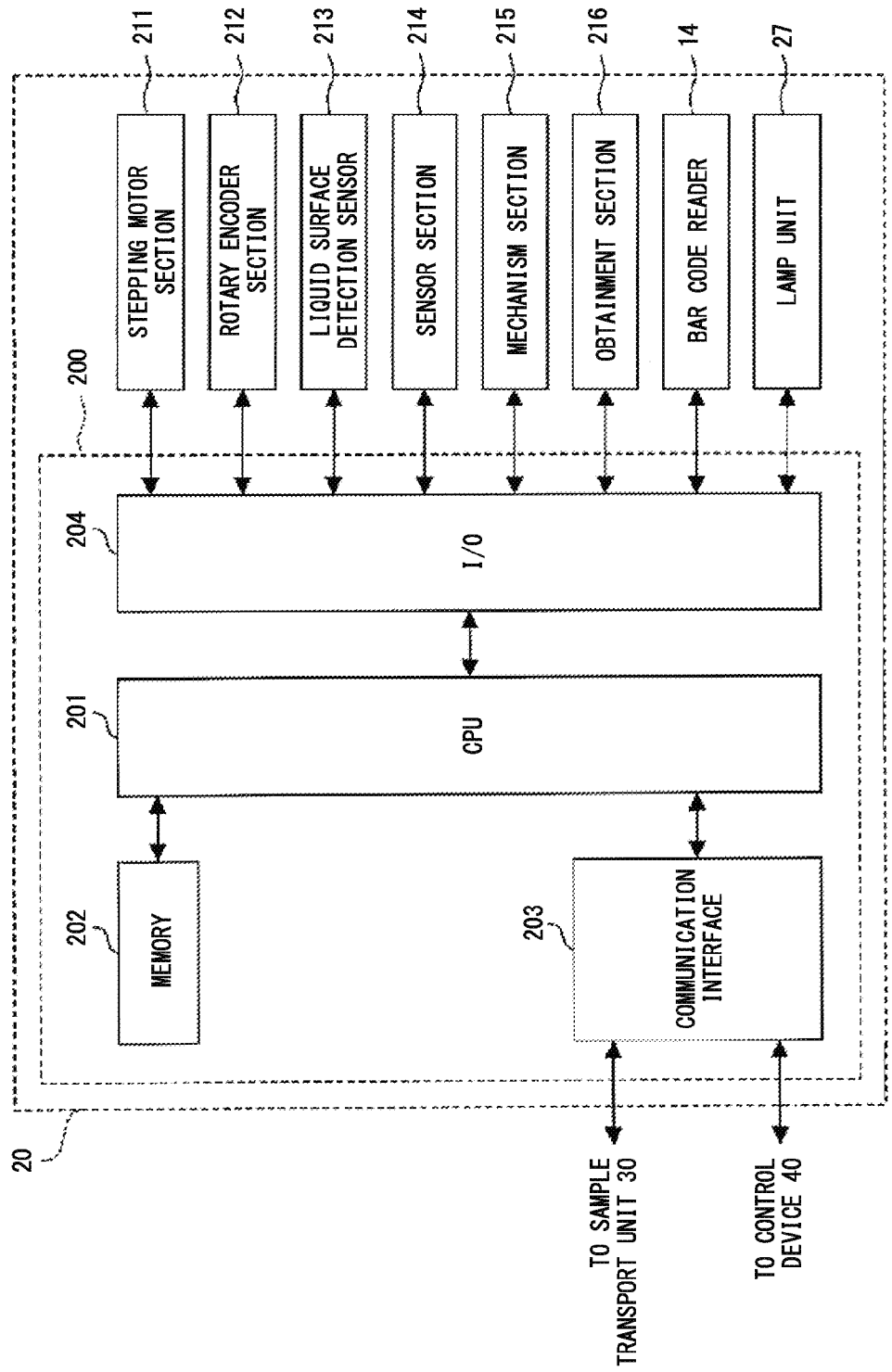
FIG. 4 shows a configuration of the measurement unit of the blood sample analyzer.

As shown in FIG. 4, the measurement unit 20 includes a control section 200, a stepping motor section 211, a rotary encoder section 212, the liquid surface detection sensor 213, a sensor section 214, a mechanism section 215, an obtainment section 216, the bar code reader 14, and the lamp unit 27. The control section 200 includes a CPU 201, a memory 202, a communication interface 203, and an I/O interface 204.

The CPU 201 executes a computer program stored in the memory 202. The memory 202 is formed by a ROM, a RAM, a hard disk, and the like. The CPU 201 drives the sample transport unit 30 via the communication interface 203. The CPU 201 transmits/receives instruction signals and data to/from the control device 40. The CPU 201 controls components in the measurement unit 20 via the I/O interface 204, and receives signals outputted from the components.

The stepping motor section 211 includes stepping motors for respectively driving the reagent tables 11 and 12, the cuvette table 13, the catcher 16, the sample dispensing arm 17, the reagent dispensing arm 18, and the cuvette transfer unit 23. The rotary encoder section 212 includes rotary encoders which output pulse signals in accordance with the amounts of rotational displacements of the respective stepping motors included in the stepping motor section 211.

The liquid surface detection sensor 213 is connected to the pipette 18a provided at the tip of the reagent dispensing arm 18. The liquid surface detection sensor 213 detects that the lower end of the pipette 18a has come into contact with the liquid surface of a reagent. The sensor section 214 includes a sensor which detects that the position in the up-down direction of the pipette 18a has been set at the origin position, and a sensor which detects that the power button 2d has been pressed. The mechanism section 215 includes: mechanisms for driving the cuvette supply unit 15, the urgent sample setting part 19, the heating unit 24, and the fluid unit 26; and pneumatic sources which supply pressure to the piercer 17a and the pipette 18a so that the piercer 17a and the pipette 18a can perform dispensing operations. The obtainment section 216 includes the detection unit 22.

As shown in FIG. 2, the control device 40 is composed of the display unit 41, an input unit 42, and a computer body 43. The control device 40 receives optical information from the measurement unit 20. The processor of the control device 40 executes a computer program for blood sample determination, based on the optical information.

Figure 5:
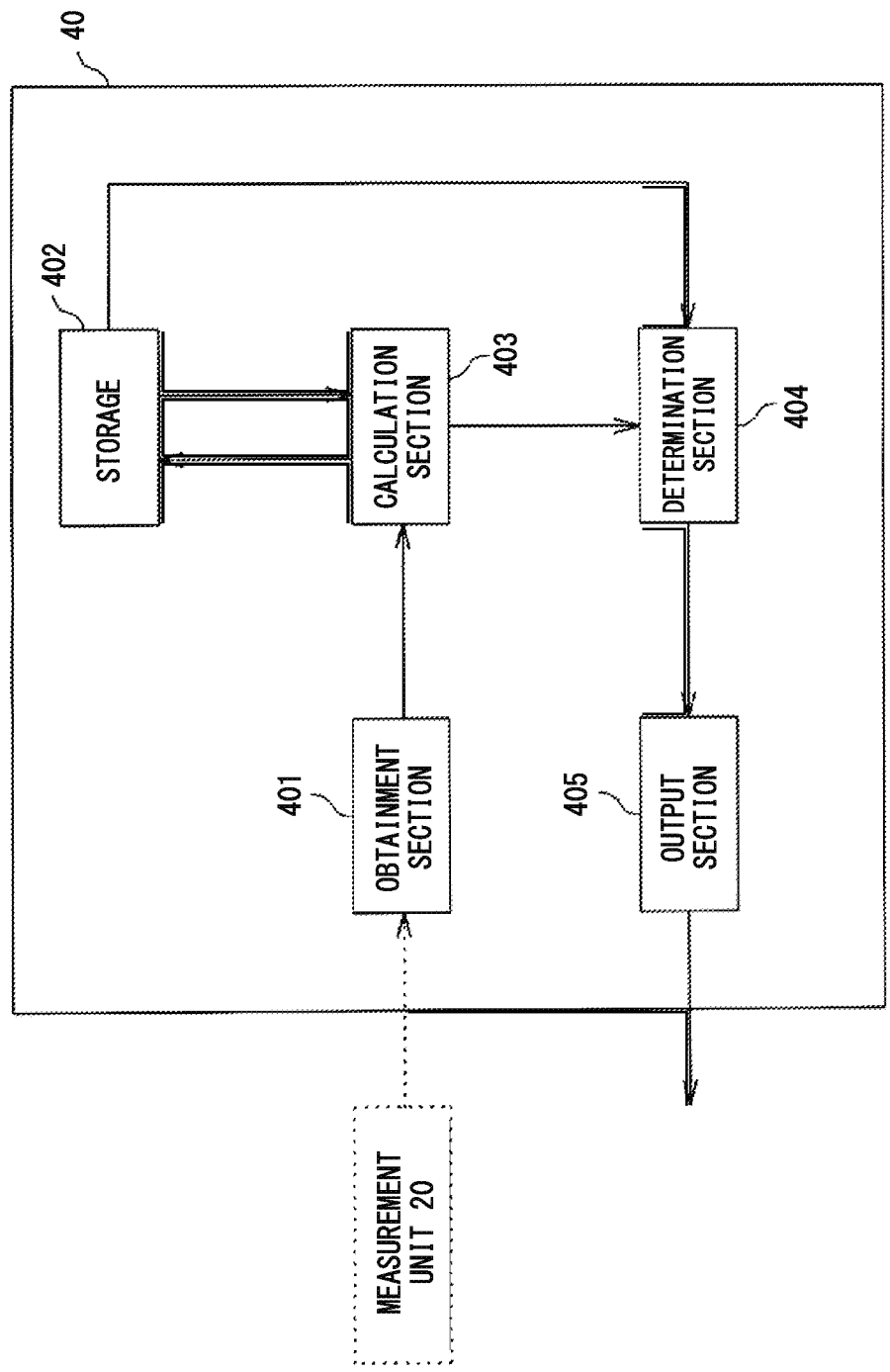
FIG. 5 shows a functional configuration of a control device of the blood sample analyzer.

FIG. 5 shows a functional configuration of the control device 40. As shown in FIG. 5, the control device 40 includes an obtainment section 401, a storage 402, a calculation section 403, a determination section 404, and an output section 405. The obtainment section 401 is communicably connected to the measurement unit 20 via a network.

The obtainment section 401 obtains optical information transmitted from the measurement unit 20. The storage 402 has stored therein predetermined thresholds necessary for determination, equations for calculating values of various types of parameters regarding derivative of clot waveform, and the like. The storage 402 may also have stored therein equations for calculating clotting time. The calculation section 403 calculates values of various types of parameters, in accordance with the equations stored in the storage 402, by use of the information obtained by the obtainment section 401. The determination section 404 determines whether the values of the parameters calculated by the calculation section 403 are smaller than their corresponding predetermined thresholds stored in the storage 402. The output section 405 outputs the result of the determination made by the determination section 404, as reference information about the blood sample.

Figure 6:
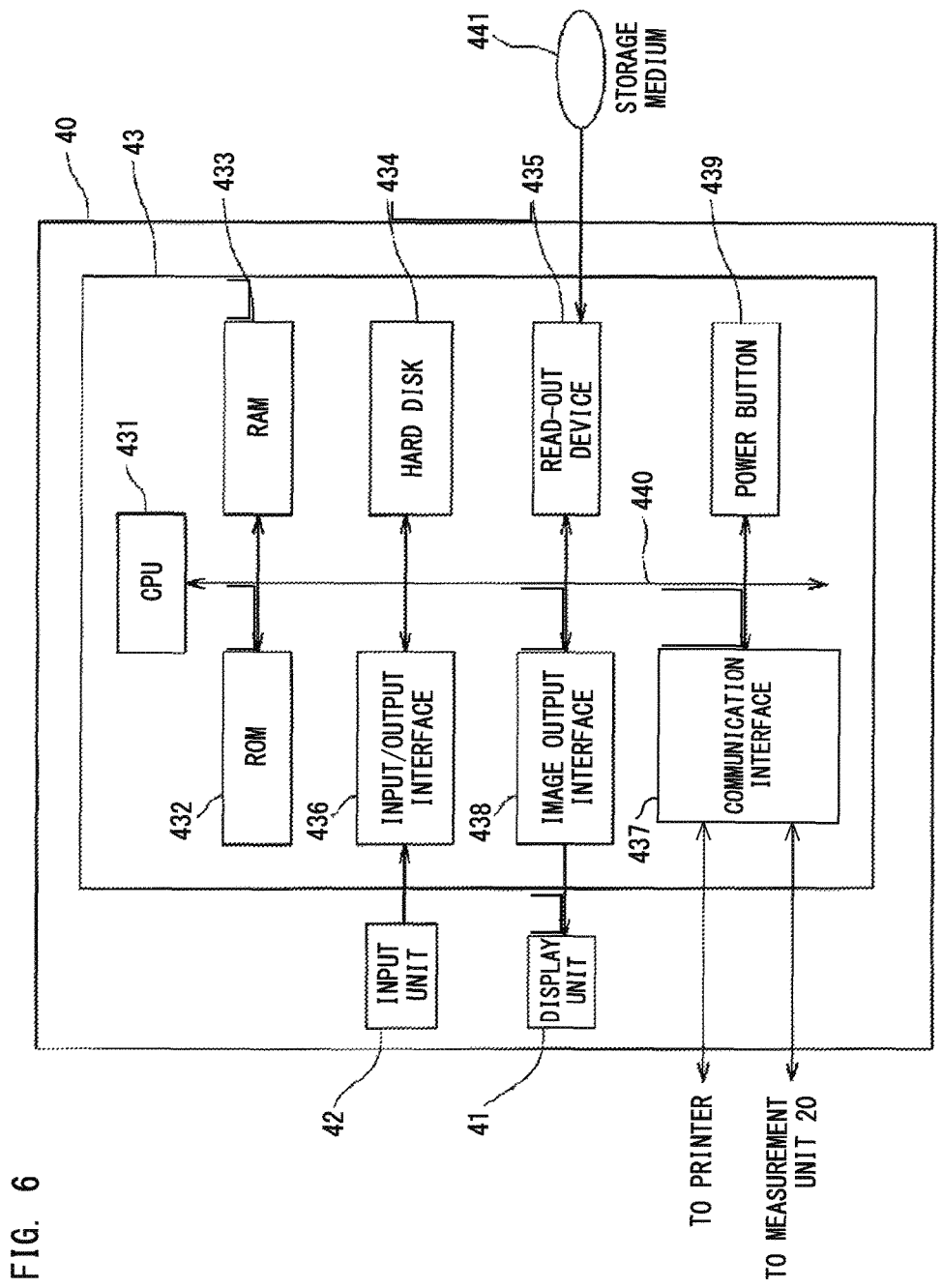
FIG. 6 shows a hardware configuration of a control device of the blood sample analyzer.

As shown in FIG. 6, the computer body 43 of the control device 40 includes a CPU 431, a ROM 432, a RAM 433, the hard disk 434, a read-out device 435, an input/output interface 436, a communication interface 437, an image output interface 438, and a power button 439. The CPU 431, the ROM 432, the RAM 433, the hard disk 434, the read-out device 435, the input/output interface 436, the communication interface 437, the image output interface 438, and the power button 439 are communicably connected to one another via a bus 440.

The CPU 431 executes computer programs stored in the ROM 432 and computer programs loaded on the RAM 433. By the CPU 431 executing application programs, the function blocks described above are realized. Accordingly, the computer system functions as a terminal being a determination apparatus for blood sample determination.

The ROM 432 is formed by a mask ROM, a PROM, an EPROM, an EEPROM, or the like. The ROM 432 has stored therein computer programs to be executed by the CPU 431, and data to be used therefor.

The RAM 433 is formed by an SRAM, a DRAM, or the like. The RAM 433 is used for reading out computer programs stored in the ROM 432 and the hard disk 434. The RAM 433 is also used as a work area for the CPU 431 when the CPU 431 executes these computer programs.

The hard disk 434 has installed therein an operating system, computer programs such as an application program (computer program for blood sample determination) to be executed by the CPU 431, data to be used in execution of the computer programs, and the settings of the control device 40.

The read-out device 435 is formed by a flexible disk drive, a CD-ROM drive, a DVD-ROM drive, and the like. The read-out device 435 can read out computer programs or data stored in a portable storage medium 441 such as a CD or a DVD.

The input/output interface 436 is formed by: for example, serial interfaces such as USB, IEEE1394, and RS-232C; parallel interfaces such as SCSI, IDE, and IEEE1284; and analog interfaces such as a D/A converter and an A/D converter. The input unit 42 such as a keyboard and a mouse is connected to the input/output interface 436. The user inputs an instruction via the input unit 42, and the input/output interface 436 receives a signal inputted via the input unit 42.

The communication interface 437 is, for example, an Ethernet (registered trademark) interface or the like. The control device 40 can transmit print data to a printer via the communication interface 437. The communication interface 437 is connected to the measurement unit 20. The CPU 431 transmits/receives instruction signals and data to/from the measurement unit 20 via the communication interface 437.

The image output interface 438 is connected to the display unit 41 which is formed by an LCD or a CRT. The image output interface 438 outputs an image signal in accordance with image data to the display unit 41. The display unit 41 displays an image based on the image signal outputted from the image output interface 438.

With reference to FIG. 4, during measurement operation, the CPU 201 of the measurement unit 20 temporarily stores, in the memory 202, data (optical information) obtained by digitizing the detection signal outputted from the detection unit 22 (see FIG. 3). The storage area of the memory 202 is divided into areas so as to correspond to the respective support parts 22a. In each area, data (optical information) is sequentially stored which is obtained when light of a predetermined wavelength is emitted to a cuvette 104 supported in its corresponding support part 22a. Thus, data is sequentially stored in the memory 202 for a predetermined measurement time period. When the measurement time period has elapsed, the CPU 201 stops storing data into the memory 202. Then, the CPU 201 transmits the stored data to the control device 40 via the communication interface 203. The control device 40 processes the received data to conduct analysis, and displays the analysis result on the display unit 41.

Figure 7:
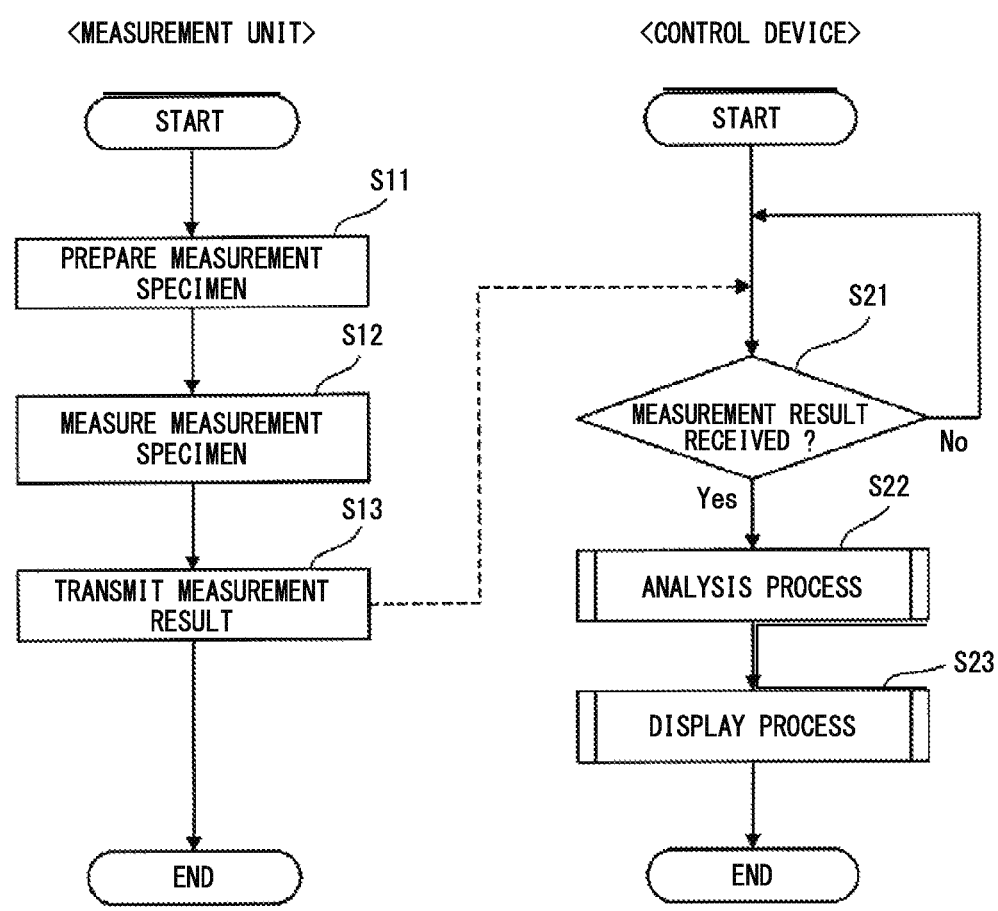
FIG. 7 is a flow chart showing a measurement process of a blood sample performed by the blood sample analyzer.

The processing in the measurement unit 20 is performed mainly under control of the CPU 201 of the measurement unit 20. The processing in the control device 40 is performed mainly under control of the CPU 431 of the control device 40. With reference to FIG. 7, upon start of the measurement process, as described above, the measurement unit 20 aspirates a blood sample (plasma) from a sample container 101, and dispenses the aspirated blood sample into an empty cuvette 104 on the cuvette table 13. Then, the measurement unit 20 transfers, to the heating unit 24, the cuvette 104 into which the blood sample has been dispensed. Then, the measurement unit 20 heats the blood sample in the cuvette 104 to a predetermined temperature (37° C., for example). Then, the measurement unit 20 adds a reagent into the cuvette 104 to prepare a measurement specimen (step S11). The measurement unit 20 starts counting time from the time point of the addition of the reagent into the cuvette 104.

Then, the measurement unit 20 transfers, to the detection unit 22, the cuvette 104 into which the reagent has been added. Then, the measurement unit 20 emits light to the cuvette 104 to measure the measurement specimen (step S12). In this measurement, data based on light having a wavelength of 660 nm (the amount of scattered light or the amount of transmitted light) is sequentially stored in the memory 202 for the measurement time period. At this time, the data is stored into the memory 202, associated with the elapsed time from the reagent addition time point. When the measurement time period has elapsed, the measurement unit 20 stops the measurement. Then, the measurement unit 20 transmits the measurement result (data) stored in the memory 202, to the control device 40 (step S13). When the control device 40 has received the measurement result (data) from the measurement unit 20 (step S21: YES), the control device 40 executes an analysis process on the received measurement result (step S22). That is, with respect to the measurement specimen, the control device 40 calculates parameters (|min 1|, |min 2|, and max 2) regarding derivative of clot waveform, and makes a determination based on the parameters. It should be noted that the control device 40 may calculate the clotting time and the clot waveform of the measurement specimen. Further, the control device 40 may determine, based on the clotting time, whether prolongation of the clotting time of the measurement specimen is observed.

Figure 8A:
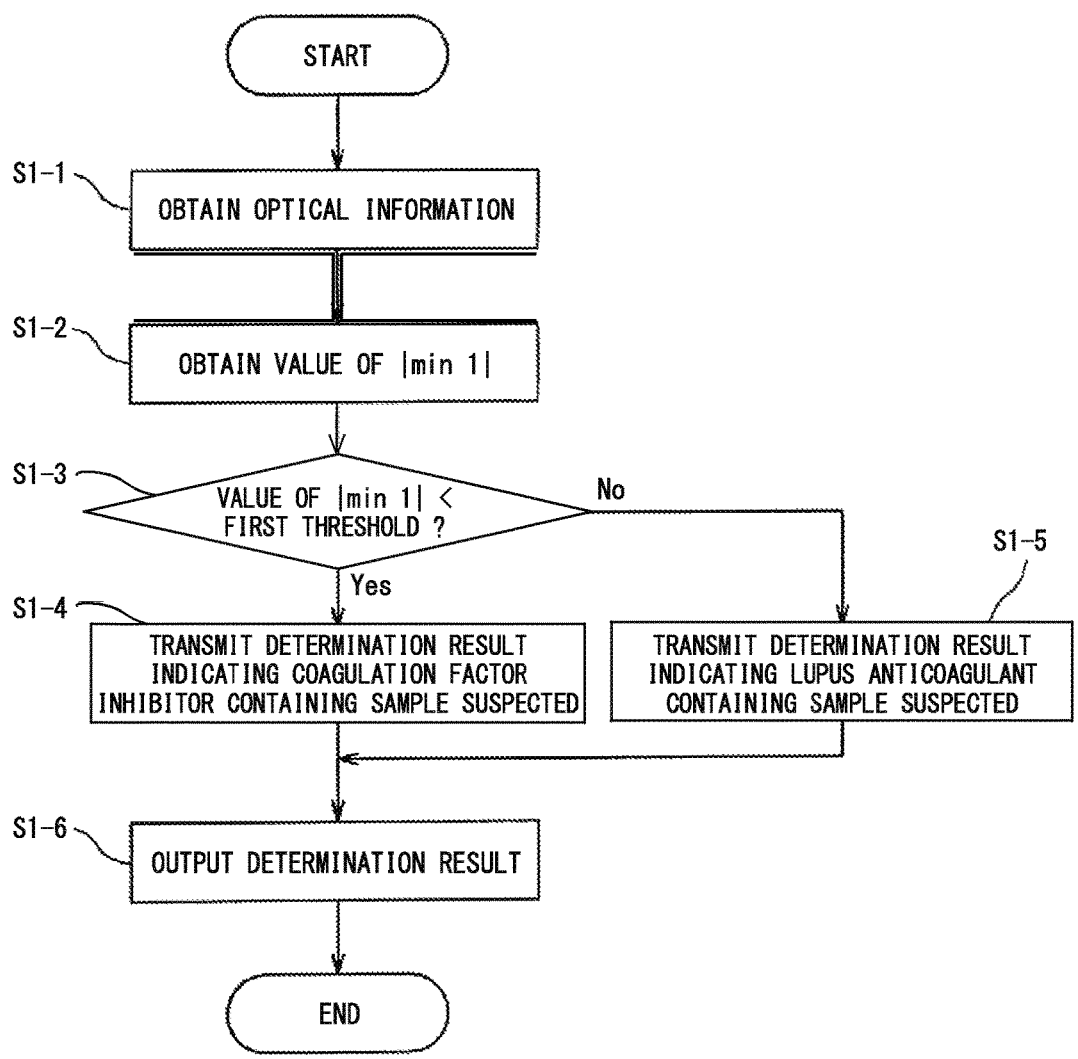
FIG. 8A is a flow chart showing an analysis process of a blood sample performed by the blood sample analyzer.

With reference to FIG. 8A, the flow of the process using one parameter regarding derivative of clot waveform will be described. Here, an example case will be described in which: based on the optical information about the amount of light obtained from the measurement specimen, the value of |min 1| is obtained as the value of the parameter regarding derivative of clot waveform; and the obtained value is compared with its corresponding predetermined threshold, thereby to make a blood sample determination. However, the present embodiment is not limited to this example only. In this example, instead of |min 1|, the value of |min 2| or max 2 may be obtained to make a determination.

First, in step S1-1, based on the data (the amount of scattered light or the amount of transmitted light) received from the measurement unit 20, the obtainment section 401 of the control device 40 obtains optical information (scattered light intensity, or transmittance or absorbance). Next, in step S1-2, from the optical information obtained by the obtainment section 401, the calculation section 403 calculates the value of |min 1| in accordance with an equation for calculating the parameter regarding derivative of clot waveform stored in the storage 402. It should be noted that the clotting time and the clot waveform are not used in the process of the determination described later. However, the calculation section 403 may further calculate the clotting time and the clot waveform from the optical information obtained by the obtainment section 401.

In step S1-3, by using the value of |min 1| calculated by the calculation section 403 and its corresponding predetermined threshold stored in the storage 402, the determination section 404 determines whether the blood sample is suspected to be a sample derived from a subject having a coagulation factor inhibitor or LA. Here, when the value of |min 1| is smaller than a first threshold, the process is advanced to step S1-4. In step S1-4, the determination section 404 transmits, to the output section 405, a determination result indicating that the blood sample is suspected to be a sample derived from a subject having a coagulation factor inhibitor. On the other hand, when the value of |min 1| is not smaller than the first threshold (that is, the value of |min 1| is greater than or equal to the first threshold), the process is advanced to step S1-5. In step S1-5, the determination section 404 transmits, to the output section 405, a determination result indicating that the blood sample is suspected to be a sample derived from a subject having LA. It should be noted that in a case where the value of |min 2| is used, the value of |min 2| is compared with a second threshold, and in a case where the value of max 2 is used, the value of max 2 is compared with a third threshold.

In step S1-6, the output section 405 outputs the determination result to be displayed on the display unit 41 or printed by a printer. Alternatively, the output section 405 may output the determination result in sound. Accordingly, the determination result can be provided to the user as reference information about the blood sample.

Figure 8B:
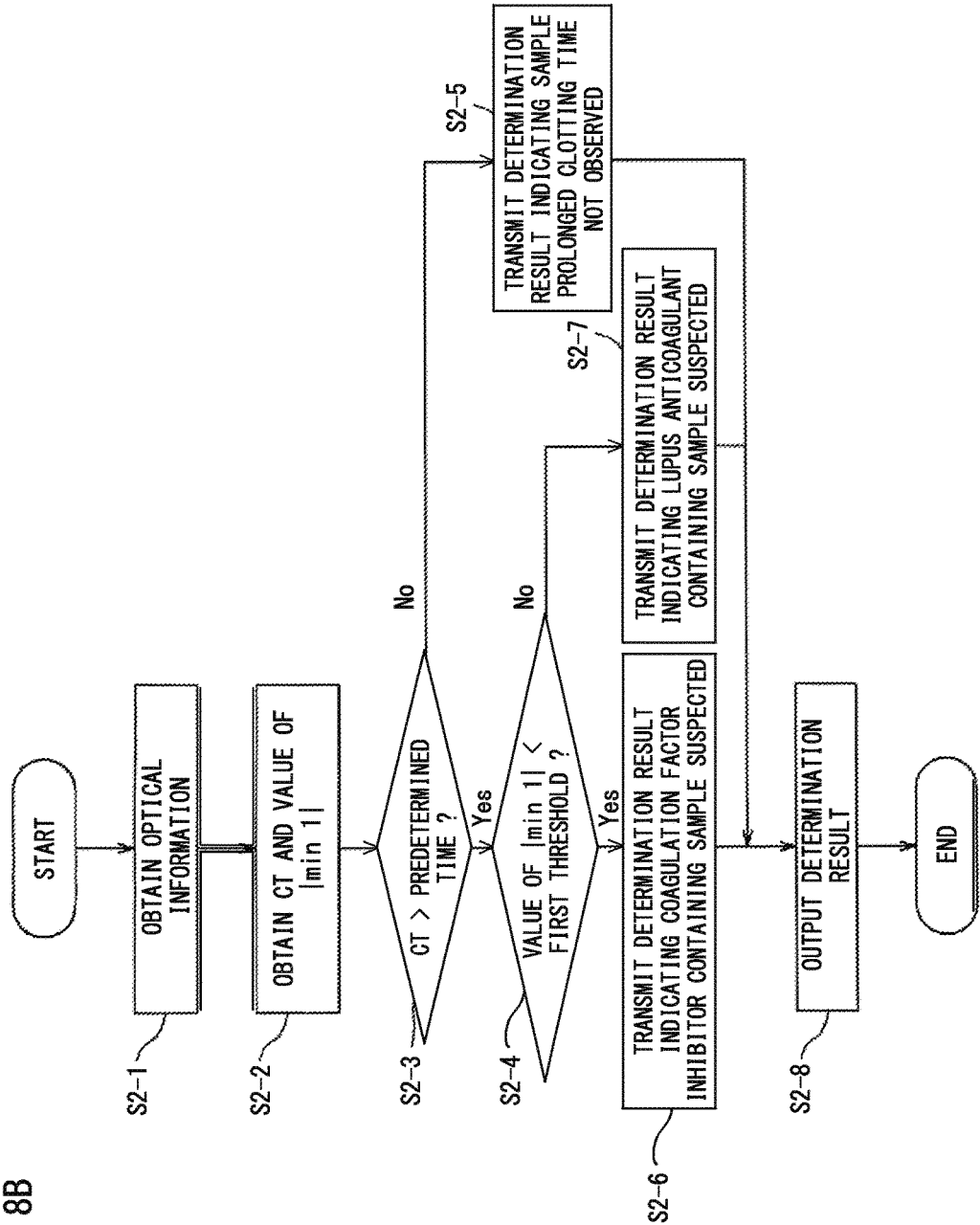
FIG. 8B is a flow chart showing an analysis process of a blood sample performed by the blood sample analyzer.

The flow of the process shown in FIG. 8A further including a step of comparing the clotting time with a predetermined time will be described with reference to FIG. 8B. Here, an example case will be described in which: the clotting time and the value of |min 1| are obtained from the optical information about the amount of light from the measurement specimen; and when the clotting time is longer than a predetermined time, the obtained value of the parameter is compared with its corresponding predetermined threshold, thereby to make a blood sample determination. However, the present embodiment is not limited to this example only. In this example, instead of |min 1|, the value of |min 2| or max 2 may be obtained to make a determination.

First, in step S2-1, based on the data received from the measurement unit 20, the obtainment section 401 of the control device 40 obtains optical information. Next, in step S2-2, from the optical information obtained by the obtainment section 401, the calculation section 403 calculates the clotting time (hereinafter, also referred to as "CT") and the value of |min 1|, in accordance with an equation for calculating the clotting time stored in the storage 402 and an equation for calculating the parameter regarding derivative of clot waveform. The calculation section 403 may further calculate the clot waveform from the optical information obtained by the obtainment section 401.

In step S2-3, the determination section 404 compares the CT calculated by the calculation section 403 with a predetermined time. Here, the predetermined time may be a clotting time of a normal sample stored in advance in the storage 402, or may be a clotting time calculated by measuring a normal sample in the same manner as in the case of the blood sample. In step S2-3, when the CT is longer than the predetermined time, the process is advanced to step S2-4. On the other hand, the CT is not longer than the predetermined time (that is, the CT is shorter than or equal to the predetermined time), the process is advanced to step S2-5. In step S2-5, the determination section 404 transmits, to the output section 405, a determination result indicating that the blood sample is a sample for which prolongation of the clotting time is not observed.

In step S2-4, the determination section 404 compares the value of |min 1| calculated by the calculation section 403 with the first threshold stored in the storage 402. When the value of |min 1| is smaller than the first threshold, the process is advanced to step S2-6. In step S2-6, the determination section 404 transmits, to the output section 405, a determination result indicating that the blood sample is suspected to be a sample derived from a subject having a coagulation factor inhibitor.

On the other hand, in step S2-4, when the value of |min 1| is not smaller than the first threshold (that is, the value of |min 1| is greater than or equal to the first threshold), the process is advanced to step S2-7. In step S2-7, the determination section 404 transmits, to the output section 405, a determination result indicating that the blood sample is suspected to be a sample derived from a subject having LA.

In step S2-8, the output section 405 outputs the determination result to be displayed on the display unit 41 or printed by a printer. Alternatively, the output section 405 may output the determination result in sound. Accordingly, the determination result can be provided to the user as reference information about the blood sample.

Figure 8C:
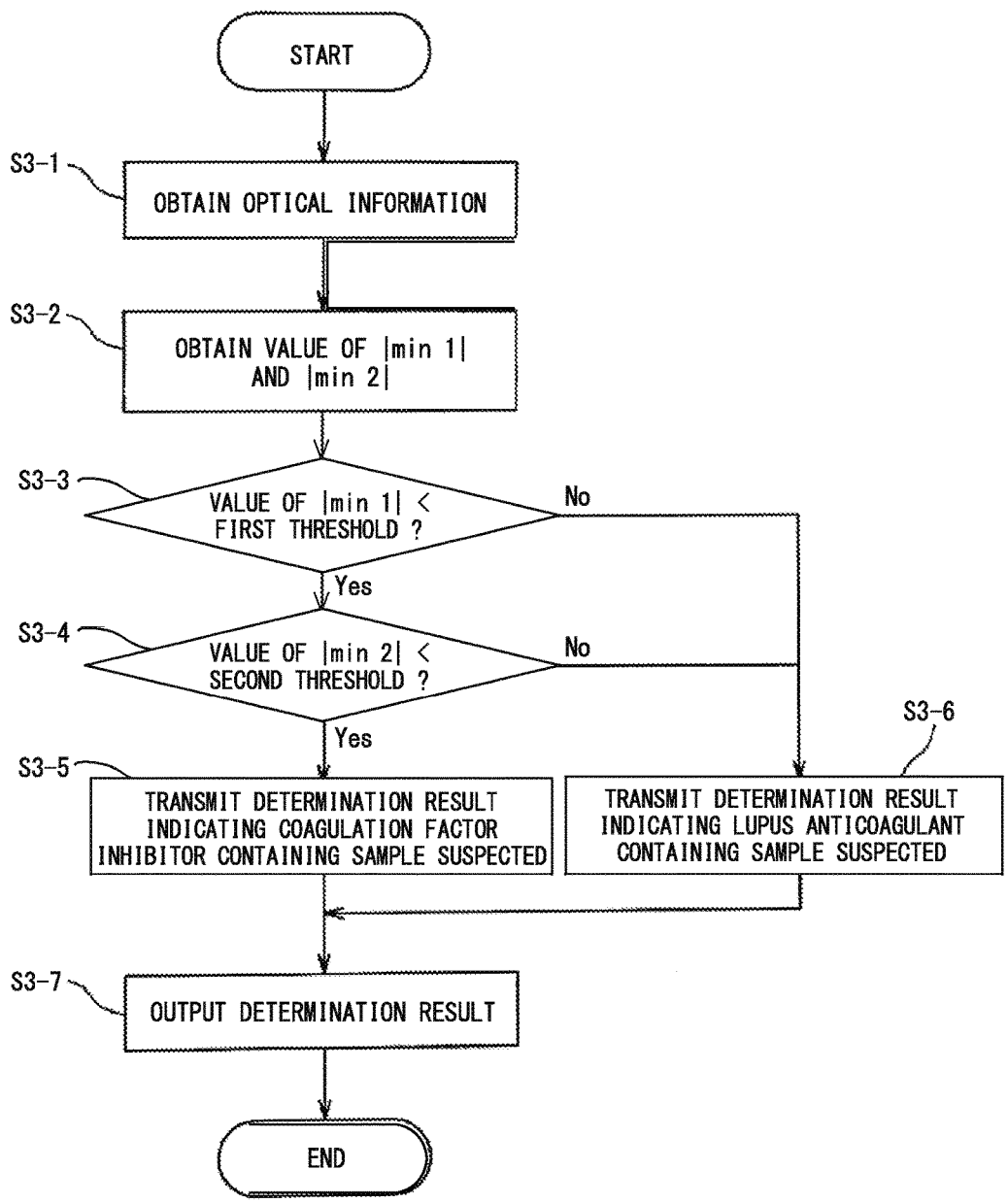
FIG. 8C is a flow chart showing an analysis process of a blood sample performed by the blood sample analyzer.

With reference to FIG. 8C, the flow of the process using two parameters regarding derivative of clot waveform will be described. Here, an example case will be described in which: based on the optical information about the amount of light from the measurement specimen, the values of |min 1| and |min 2| are obtained; and the obtained values are compared with their corresponding predetermined thresholds, thereby to make a blood sample determination. However, the present embodiment is not limited to this example only. In this example, instead of either one of |min 1| and |min 2|, the value of max 2 may be obtained to make a determination. Alternatively, in this example, the process may further include a step of comparing the clotting time with a predetermined time. Then, when the clotting time is longer than the predetermined time, the obtained values of the parameters may be compared with their corresponding predetermined thresholds, thereby to make a blood sample determination; and when the clotting time is shorter than or equal to the predetermined time, a determination result may be outputted which indicates that the blood sample is a sample for which prolongation of the clotting time is not observed.

First, in step S3-1, based on the data received from the measurement unit 20, the obtainment section 401 of the control device 40 obtains optical information. Next, in step S3-2, from the optical information obtained by the obtainment section 401, the calculation section 403 calculates the values of |min 1| and |min 2|, in accordance with equations for calculating the parameters regarding derivative of clot waveform stored in the storage 402. The calculation section 403 may further calculate the clotting time and the clot waveform from the optical information obtained by the obtainment section 401.

In step S3-3, the determination section 404 compares the value of |min 1| calculated by the calculation section 403 with the first threshold stored in the storage 402. When the value of |min 1| is smaller than the first threshold, the process is advanced to step S3-4. In step S3-4, the determination section 404 compares the value of |min 2| calculated by the calculation section 403 with the second threshold stored in the storage 402. When the value of |min 2| is smaller than the second threshold, the process is advanced to step S3-5. In step S3-5, the determination section 404 transmits, to the output section 405, a determination result indicating that the blood sample is suspected to be a sample derived from a subject having a coagulation factor inhibitor.

On the other hand, in step S3-3, when the value of |min 1| is not smaller than the first threshold (that is, the value of |min 1| is greater than or equal to the first threshold), the process is advanced to step S3-6. In step S3-4, when the value of |min 2| is not smaller than the second threshold (that is, the value of |min 2| is greater than or equal to the second threshold), the process is advanced to step S3-6. In step S3-6, the determination section 404 transmits, to the output section 405, a determination result indicating that the blood sample is suspected to be a sample derived from a subject having LA. It should be noted that, in the present embodiment, the order of the processes of step S3-3 and step S3-4 may be switched with each other as desired.

In step S3-7, the output section 405 outputs the determination result to be displayed on the display unit 41 or printed by a printer. Alternatively, the output section 405 may output the determination result in sound. Accordingly, the determination result can be provided to the user as reference information about the blood sample.

Figure 8D:
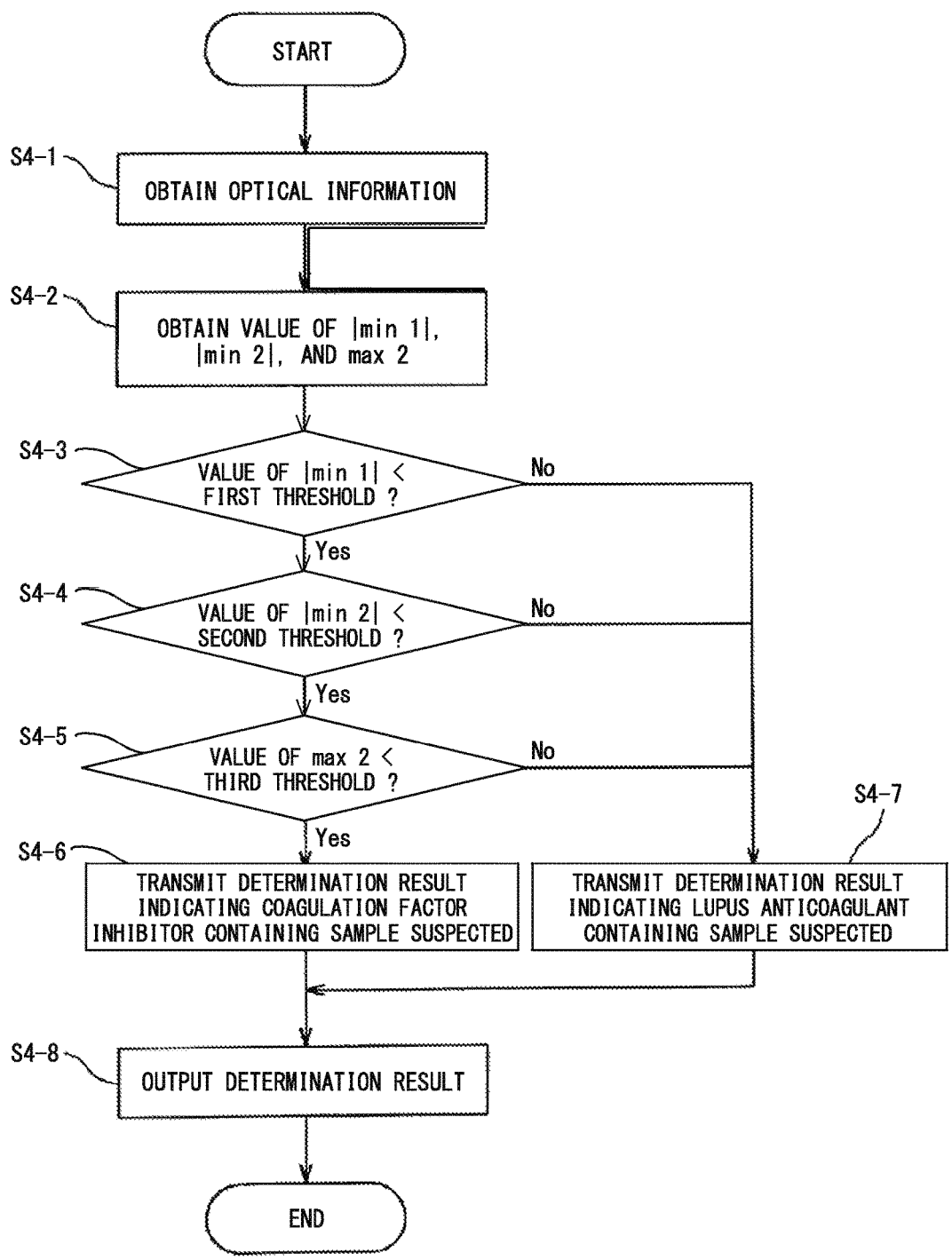
FIG. 8D is a flow chart showing an analysis process of a blood sample performed by the blood sample analyzer.

With reference to FIG. 8D, the flow of the process using three parameters regarding derivative of clot waveform will be described. Here, an example case will be described in which: based on the optical information about the amount of light from the measurement specimen, the values of |min 1|, |min 2|, and max 2 are obtained; and the obtained values are compared with their corresponding predetermined thresholds, thereby to make a blood sample determination. However, the present embodiment is not limited to this example only. In this example, the process may further include a step of comparing the clotting time with a predetermined time. Then, when the clotting time is longer than the predetermined time, the obtained values of the parameters may be compared with their corresponding predetermined thresholds, to make a blood sample determination; and when the clotting time is shorter than or equal to the predetermined time, a determination result may be outputted which indicates that the blood sample is a sample for which prolongation of the clotting time is not observed.

First, in step S4-1, based on the data received from the measurement unit 20, the obtainment section 401 of the control device 40 obtains optical information. Next, in step S4-2, from the optical information obtained by the obtainment section 401, the calculation section 403 calculates the values of |min 1|, |min 2|, and max 2, in accordance with equations for calculating the parameters regarding derivative of clot waveform stored in the storage 402. The calculation section 403 may further calculate the clotting time and the clot waveform from the optical information obtained by the obtainment section 401.

In step S4-3, the determination section 404 compares the value of |min 1| calculated by the calculation section 403 with the first threshold stored in the storage 402. When the value of |min 1| is smaller than the first threshold, the process is advanced to step S4-4. In step S4-4, the determination section 404 compares the value of |min 2| calculated by the calculation section 403 with the second threshold stored in the storage 402. When the value of |min 2| is smaller than the second threshold, the process is advanced to step S4-5. In step S4-5, the determination section 404 compares the value of max 2 calculated by the calculation section 403 with the third threshold stored in the storage 402. When the value of max 2 is smaller than the third threshold, the process is advanced to step S4-6. In step S4-6, the determination section 404 transmits, to the output section 405, a determination result indicating that the blood sample is suspected to be a sample derived from a subject having a coagulation factor inhibitor.

On the other hand, in step S4-3, when the value of |min 1| is not smaller than the first threshold (that is, the value of |min 1| is greater than or equal to the first threshold), the process is advanced to step S4-7. In step S4-4, when the value of |min 2| is not smaller than the second threshold (that is, the value of |min 2| is greater than or equal to the second threshold), the process is advanced to step S4-7. In step S4-5, when the value of max 2 is not smaller than the third threshold (that is, the value of max 2 is greater than or equal to the third threshold), the process is advanced to step S4-7. In step S4-7, the determination section 404 transmits, to the output section 405, a determination result indicating that the blood sample is suspected to be a sample derived from a subject having LA. It should be noted that, in the present embodiment, the order of the processes of step S4-3, step S4-4, and step S4-5 may be changed with one another as desired.

In step S4-8, the output section 405 outputs the determination result to be displayed on the display unit 41 or printed by a printer. Alternatively, the output section 405 may output the determination result in sound. Accordingly, the determination result can be provided to the user as reference information about the blood sample.

Figure 9:
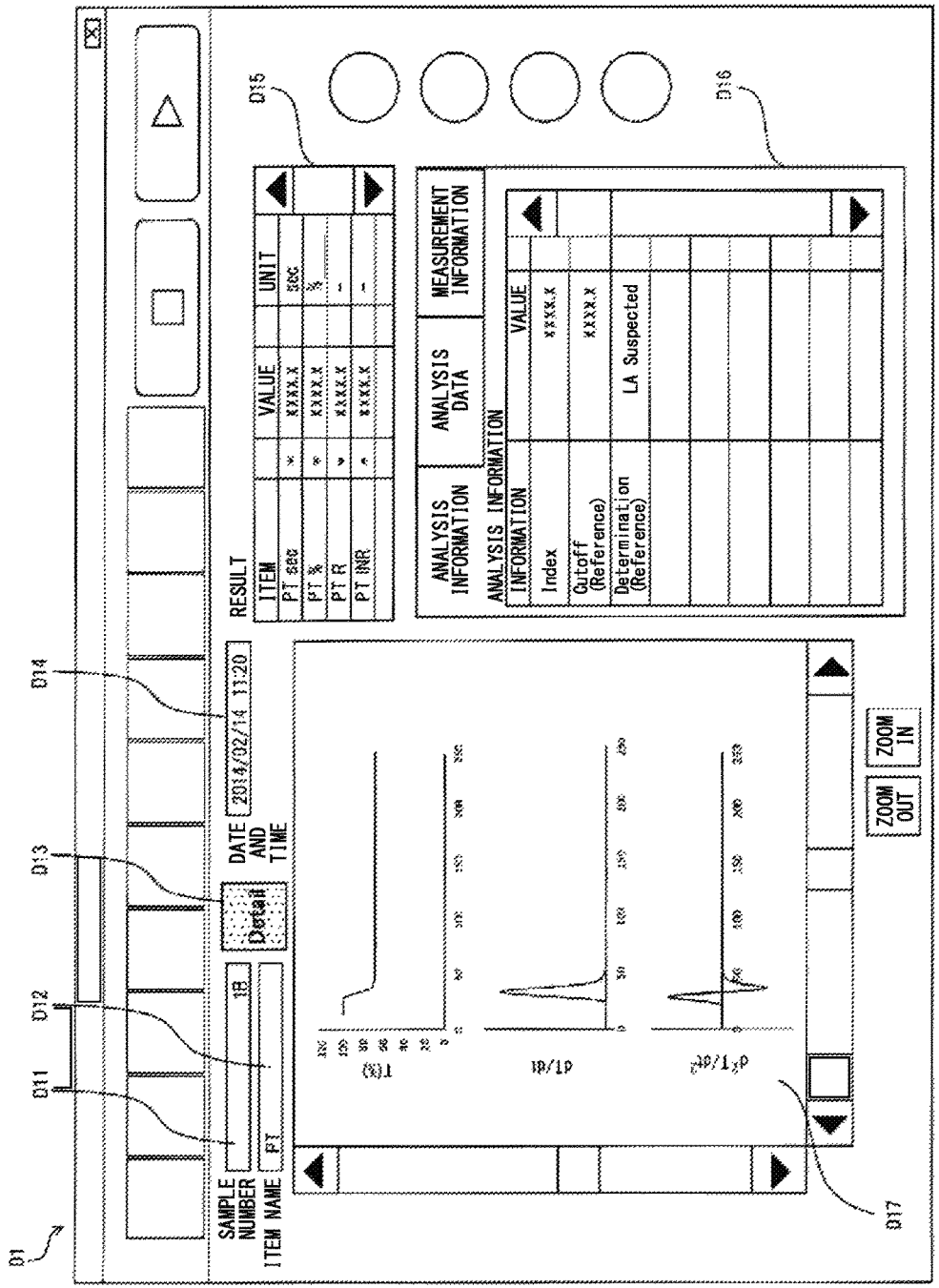
FIG. 9 shows one example of a screen on which to display an analysis result by the blood sample analyzer.

As one example of the screen on which to display the analysis result, a screen having displayed thereon a result of analysis performed on the coagulation process of a blood sample by use of a prothrombin time measuring reagent will be described with reference to FIG. 9. A screen D1 includes a region D11 for displaying a sample number, a region D12 for displaying a measurement item name, a button D13 for displaying a detailed screen, a region D14 for displaying measurement date and time, a region D15 for displaying a measurement result, a region D16 for displaying analysis information, and a region D17 for displaying a clot waveform and graphs obtained by calculating the derivative of the clot waveform.

In the region D15, measurement items and measured values are displayed. In the region D15, "PT sec" is prothrombin time. In addition to the prothrombin time (PT sec), values (PT %, PT R, PT INR) which are predetermined parameter values converted from the prothrombin time may be displayed in the region D15.

In the region D16, analysis items and reference information are displayed. In the region D16, "Index" is the value of the parameter regarding derivative of clot waveform used in the determination. "Cutoff (reference)" is a predetermined threshold that corresponds to the parameter value used in the determination. "Determination (reference)" is the determination result by the blood analyzer, and indicates that the blood sample is suspected to be a sample derived from a subject having either a coagulation factor inhibitor or LA. It is desired that disease diagnosis is performed in consideration of not only this determination result but also information of other test results. Therefore, in order to show that the predetermined thresholds and the determination result by the blood analyzer according to the present embodiment are reference information, the word "reference" is displayed. In FIG. 9, the determination result is displayed in characters "LA suspected", but the determination result may be indicated by means of a figure or a symbol such as a flag. Alternatively, the determination result may be outputted in sound.

Examples will be described below, but the above embodiments are not limited to these Examples.

EXAMPLES

Example 1: Blood Sample Determination by Clot Waveform Analysis

It was examined whether LA positive samples can be distinguished from coagulation factor inhibitor positive samples based on parameters regarding derivative of clot waveform.

(1) Reagent and Sample

As the clotting time measuring reagent, Thrombocheck APTT-SLA being an APTT reagent (Sysmex Corporation) and Thrombocheck 20 mM calcium chloride solution (Sysmex Corporation) were used. As the test plasma, plasma of LA positive patients (8 cases) and plasma of factor VIII inhibitor positive patients (5 cases) were used. As the normal plasma, CRYOcheck Pooled Normal Plasma (Precision Bio-Logic Inc) which is normal plasma for cross-mixing test was used. As the control specimen for quality control, COAGTROL IX and COAGTROL IIX (Sysmex Corporation) were used.

(2) Measurement of Sample

Each sample (50 μL) was dispensed into a reaction cuvette, and heated at 37° C. for |minute. To the reaction cuvette, the above APTT reagent (50 μL) heated at 37° C. in advance was added, and the mixture was caused to react at 37° C. for 3 minutes. Then, the 20 mM calcium chloride solution (50 μL) was added to the mixture, and the transmittance was continuously measured for 420 seconds. For the measurement, a fully automated blood coagulation measurement apparatus CS-2400 (Sysmex Corporation) was used.

(3) Analysis Result

Based on the temporal change of the obtained transmittance, |min 1|, |min 2|, and max 2 were calculated as the parameters regarding derivative of clot waveform. The ratios of the values of |min 1|, |min 2|, and max 2 of each test plasma to the values of |min 1|, |min 2|, and max 2 of the normal plasma were calculated and plotted on graphs. The obtained graphs are shown in FIGS. 10A to 10C.

Figure 10A:
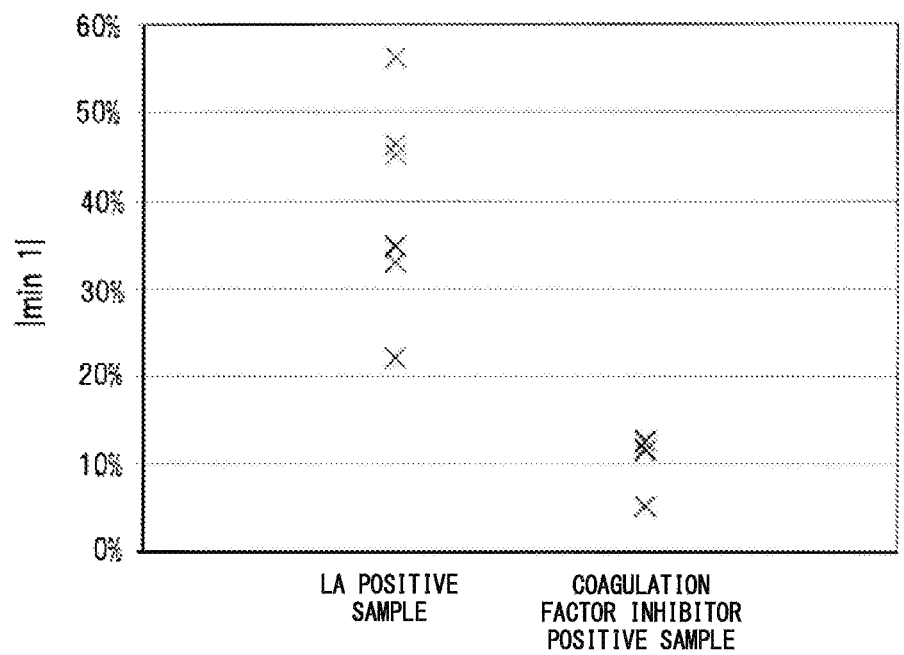
FIG. 10A is a graph showing the ratio of the value of |min 1| of each test plasma to the value of |min 1| of normal plasma.
Figure 10B:
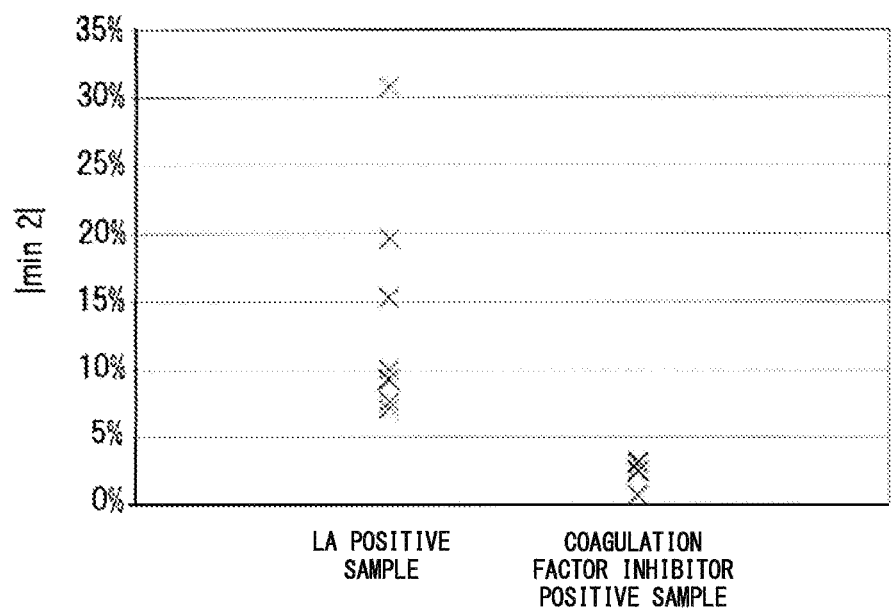
FIG. 10B is a graph showing the ratio of the value of |min 2| of each test plasma to the value of |min 2| of normal plasma.
Figure 10C:
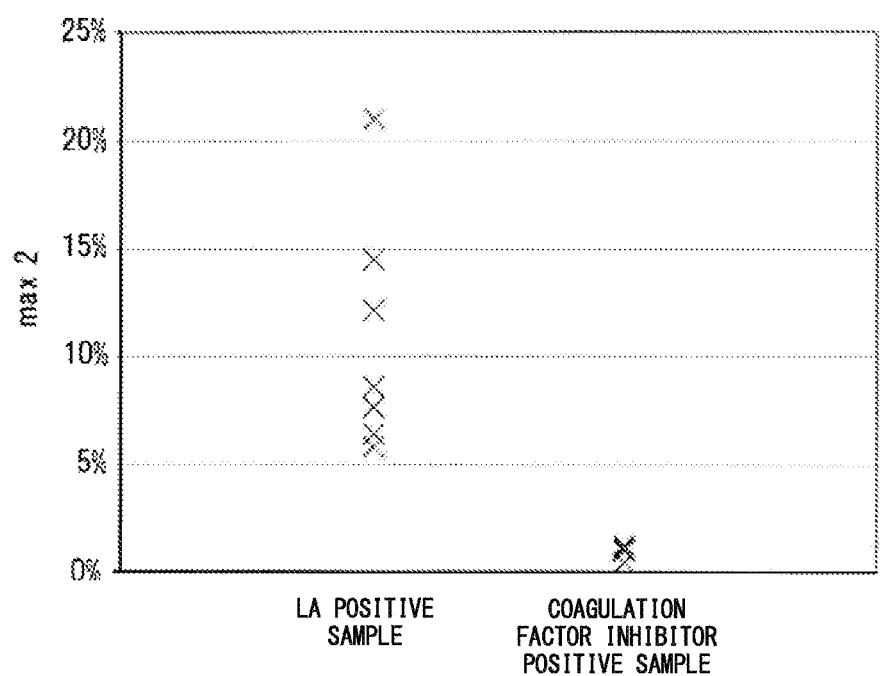
FIG. 10C is a graph showing the ratio of the value of max 2 of each test plasma to the value of max 2 of normal plasma.

As shown in FIGS. 10A to 10C, with respect to each of |min 1|, |min 2|, and max 2, the LA positive sample group showed higher values than those of the coagulation factor inhibitor positive sample group. Also with respect to each of |min 1|, |min 2|, and max 2, there is a gap between the minimum value of the LA positive sample group and the maximum value of the coagulation factor inhibitor positive sample group. Thus, it is suggested that, for each parameter, a threshold can be set that separates LA positive samples from coagulation factor inhibitor positive samples. From these, it was shown that, based on parameters regarding derivative of clot waveform, it is possible to clearly distinguish LA positive samples from coagulation factor inhibitor positive samples. Since these parameters are quantitative indexes, it is considered that persons who are not experts can make a clear sample determination.

Reference Example 1: Sample Determination by Use of Graph Pattern of Cross-Mixing Test There was information that it is possible to distinguish LA positive samples from coagulation factor inhibitor positive samples, by comparing, in cross-mixing test, the degree of change in the pattern of graph obtained through immediate-type-measurement (where the clotting time is measured immediately after the normal plasma and the test plasma have been mixed), with the degree of change in the pattern of graph obtained through delayed-type-measurement (where the clotting time is measured after the normal plasma and the test plasma have been mixed together and then heated at 37° C. for two hours). Thus, this method was actually examined.

(1) Reagent and Sample

The reagent, the test plasma, the normal plasma, and the control specimen for quality control used in this Reference Example were the same as those used in Example 1.

(2) Measurement of Sample

The normal plasma and the test plasma were mixed at the ratios of 10:0, 9:1, 8:2, 5:5, 2:8, 1:9, and 0:10. The clotting time of each obtained sample was measured. In the measurement for obtaining the immediate-type-measurement graph pattern, mixing of the normal plasma and the test plasma and measurement of the clotting time were performed by CS-2400 (Sysmex Corporation). In the measurement for obtaining the delayed-type-measurement graph pattern, mixing of the normal plasma and the test plasma was performed by hand. Then, after each obtained sample was heated at 37° C. for two hours, measurement of the clotting time was performed by CS-2400 (Sysmex Corporation). The clotting time obtained for each sample was plotted on graphs having the ratio of test plasma in the sample as the X axis and the clotting time as the Y axis.

(3) Analysis Result

Figure 11A:
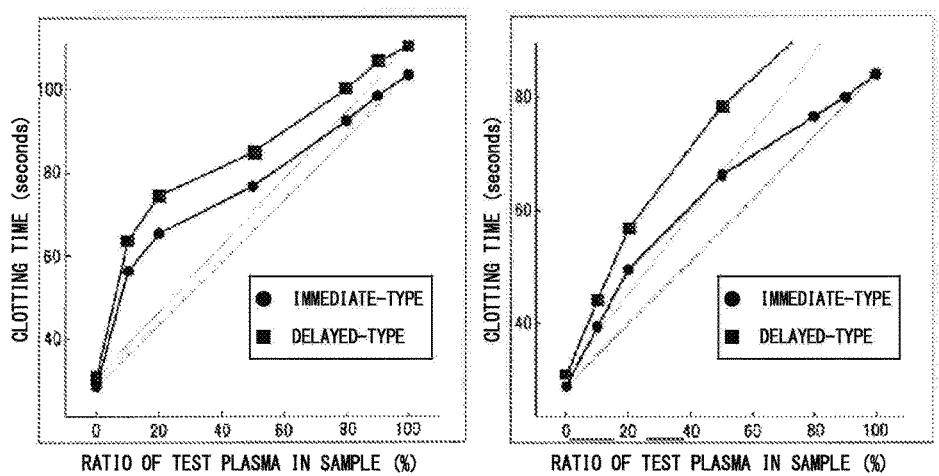
FIG. 11A is a graph showing clotting time obtained through immediate-type-measurement and delayed-type-measurement when cross-mixing test is performed on LA positive samples.
Figure 11B:
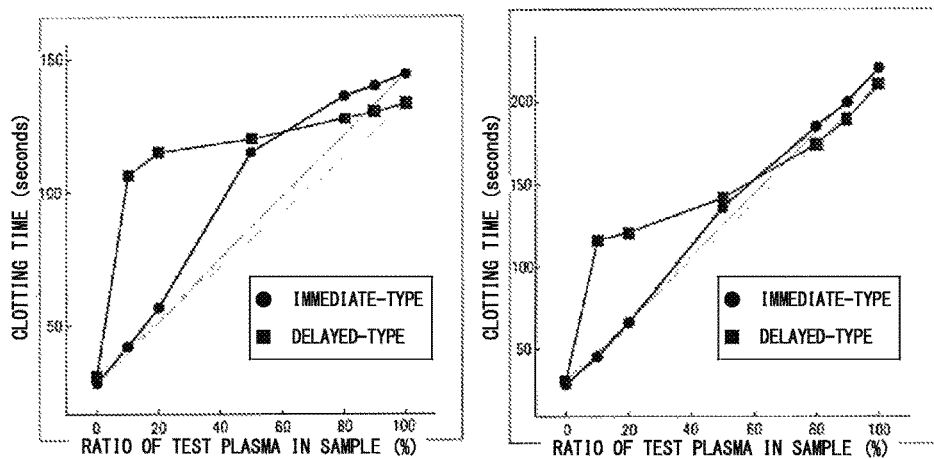
FIG. 11B is a graph showing clotting time obtained through immediate-type-measurement and delayed-type-measurement when cross-mixing test is performed on coagulation factor inhibitor positive samples.

With respect to a part of the LA positive sample group, the immediate-type-measurement and delayed-type-measurement graph patterns are shown in FIG. 11A. With respect to a part of the coagulation factor inhibitor positive sample group, the immediate-type-measurement and delayed-type-measurement graph patterns are shown in FIG. 11B. As shown in these figures, the changes in the graph patterns of the LA positive samples and the coagulation factor inhibitor positive samples were similar to each other. Thus, distinction between these based on the changes in graph patterns has to be done by qualitative assessment. Thus, it is difficult for non-expert persons to make an appropriate determination.

Reference Example 2: Sample Determination by Use of ICA

In recent years, ICA has been devised as a quantitative index for cross-mixing test, and is recommended as a method for diagnosing LA. Whether ICA can distinguish LA positive samples from coagulation factor inhibitor positive samples was examined.

(1) Reagent and Sample

The reagent, the test plasma, the normal plasma, and the control specimen for quality control used in this Reference Example were the same as those used in Example 1.

(2) Measurement of Sample

Figure 12:
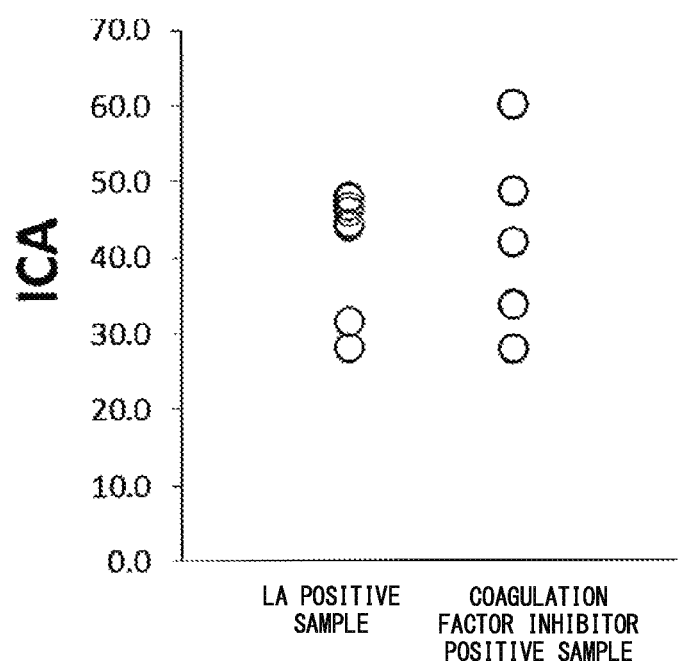
FIG. 12 is a graph showing values of ICA (the Index for circulating anticoagulant) of a LA positive sample group and a coagulation factor inhibitor positive sample group.

The normal plasma and the test plasma were mixed at the ratios of 10:0, 5:5, and 0:10. The clotting time of each obtained sample was measured. In the measurement for obtaining the immediate-type-measurement graph pattern, mixing of the normal plasma and the test plasma and measurement of the clotting time were performed by CS-2400 (Sysmex Corporation). In the measurement for obtaining the delayed-type-measurement graph pattern, mixing of the normal plasma and the test plasma was performed by hand. Then, after each obtained sample was heated at 37° C. for two hours, measurement of the clotting time was performed by CS-2400 (Sysmex Corporation). The clotting time obtained for each sample was put in the equation below to calculate ICA, and each obtained ICA was plotted on a graph. FIG. 12 shows the obtained graph.

$$ICA = (B-A)/C \times 100$$

(where A represents clotting time of normal plasma, B represents clotting time of sample prepared by mixing normal plasma and test plasma, and C represents clotting time of test plasma).

(3) Analysis Result

As shown in FIG. 12, no clear difference was observed between the ICA values of the LA positive sample group and the ICA values of the coagulation factor inhibitor positive sample group. Therefore, it is difficult to distinguish LA positive samples from coagulation factor inhibitor positive samples by means of ICA.

What is claimed is:

1. A blood sample determination method comprising:
   emitting light to a measurement specimen prepared by mixing a clotting time measuring reagent and a blood sample suspected to be derived from a subject having lupus anticoagulant or a coagulation factor inhibitor, to obtain optical information about an amount of light from the measurement specimen;
   obtaining at least one parameter regarding derivative of clot waveform, based on the obtained optical information; and
   determining, based on a value of the obtained at least one parameter, that the blood sample is suspected to be a sample derived from a subject having lupus anticoagulant, and if not, then determining that the blood sample is suspected to be a sample derived from a subject having a coagulation factor inhibitor.

2. The blood sample determination method of claim 1, wherein
   in the determining, the value of the obtained at least one parameter is compared with a predetermined threshold, and determination on the blood sample is made based on a result of the comparison.

3. The blood sample determination method of claim 1, wherein
   the optical information is an amount of scattered light, transmittance, or absorbance which has been measured continuously or intermittently, and the clot waveform is a waveform representing temporal change in the amount of scattered light, the transmittance, or the absorbance.

4. The blood sample determination method of claim 1, wherein
   the at least one parameter regarding derivative of clot waveform is at least one selected from the group consisting of maximum coagulation velocity (|min 1|), maximum coagulation acceleration (|min 2|) and maximum coagulation deceleration (max 2).

5. The blood sample determination method of claim 4, wherein
   in the determining,
   the value of |min 1| is compared with a first threshold in a case where |min 1| has been obtained, the value of |min 2| is compared with a second threshold in a case where |min 2| has been obtained, and the value of max 2 is compared with a third threshold in a case where max 2 has been obtained,
   when at least one of the values that have been obtained among |min 1|, |min 2|, and max 2 is greater than or equal to a predetermined threshold corresponding to that value, it is determined that the blood sample is suspected to be a sample derived from a subject having lupus anticoagulant, and
   when all the values that have been obtained among |min 1|, |min 2|, and max 2 are smaller than predetermined thresholds corresponding to those values, it is determined that the blood sample is suspected to be a sample derived from a subject having a coagulation factor inhibitor.

6. The blood sample determination method of claim 4, wherein
   |min 1| is obtained in the obtaining of the at least one parameter, and
   in the determining, the value of |min 1| is compared with a first threshold, and when the value of |min 1| is greater than or equal to the first threshold, it is determined that the blood sample is suspected to be a sample derived from a subject having a lupus anticoagulant, and when the value of |min 1| is smaller than the first threshold, it is determined that the blood sample is suspected to be a sample derived from a subject having a coagulation factor inhibitor.

7. The blood sample determination method of claim 4, wherein
   |min 1|, |min 2<, and max 2 are obtained in the obtaining of the at least one parameter,
   in the determining, the value of |min 1| is compared with a first threshold, the value of |min 2| is compared with a second threshold, and the value of max 2 is compared with a third threshold,
   when at least one value of |min 1|, |min 2|, and max 2 is greater than or equal to the threshold corresponding to that value, it is determined that the blood sample is suspected to be a sample derived from a subject having lupus anticoagulant, and
   when the value of |min 1| is smaller than the first threshold, the value of |min 2| is smaller than the second threshold, and the value of max 2 is smaller than the third threshold, it is determined that the blood sample is suspected to be a sample derived from a subject having a coagulation factor inhibitor.

8. The blood sample determination method of claim 1, wherein
   the clotting time measuring reagent is a reagent for measuring at least one selected from the group consisting of prothrombin time, activated partial thromboplastin time, dilute prothrombin time, dilute activated partial thromboplastin time, kaolin clotting time, dilute Russell's Viper Venom time, thrombin time, and dilute thrombin time.

9. The blood sample determination method of claim 1, wherein
   the blood sample is whole blood or plasma.

10. A blood sample determination method comprising:
    emitting light to a measurement specimen prepared by mixing a blood sample and a clotting time measuring reagent, to obtain optical information about an amount of light from the measurement specimen;
    obtaining a clotting time and obtaining at least one parameter regarding derivative of clot waveform, based on the obtained optical information; and
    with respect to a blood sample for which prolongation of the clotting time is observed, determining, based on a value of the obtained at least one parameter, that the blood sample is suspected to be a sample derived from a subject having lupus anticoagulant, and if not, then determining that the blood sample is suspected to be a sample derived from a subject having a coagulation factor inhibitor.

* * * * *